United States Patent
Hyodo et al.

(10) Patent No.: US 10,458,881 B2
(45) Date of Patent: Oct. 29, 2019

(54) PIPE EVALUATION METHOD, MEASUREMENT DEVICE, AND PIPE EVALUATION SYSTEM

(71) Applicants: NATIONAL UNIVERSITY CORPORATION TOTTORI UNIVERSITY, Tottori-shi, Tottori (JP); NATIONAL UNIVERSITY CORPORATION SHIMANE UNIVERSITY, Matsue-shi, Shimane (JP)

(72) Inventors: Masahiro Hyodo, Tottori (JP); Hidehiko Ogata, Tottori (JP); Naoki Kawamura, Tottori (JP); Tsuguhiro Nonaka, Matsue (JP); Masayuki Ishii, Matsue (JP)

(73) Assignees: NATIONAL UNIVERSITY CORPORATION TOTTORI UNIVERSITY, Tottori-shi (JP); NATIONAL UNIVERSITY CORPORATION SHIMANE UNIVERSITY, Matsue-shi (JP)

( * ) Notice: Subject to any disclaimer, the term of this patent is extended or adjusted under 35 U.S.C. 154(b) by 375 days.

(21) Appl. No.: 15/414,965

(22) Filed: Jan. 25, 2017

(65) Prior Publication Data

US 2017/0131175 A1    May 11, 2017

Related U.S. Application Data

(63) Continuation of application No. PCT/JP2015/070526, filed on Jul. 17, 2015.

(30) Foreign Application Priority Data

Jul. 25, 2014    (JP) .................................. 2014-152382

(51) Int. Cl.
    *G01M 5/00*    (2006.01)
    *G01N 3/08*    (2006.01)

(52) U.S. Cl.
    CPC ........ *G01M 5/0025* (2013.01); *G01M 5/0033* (2013.01); *G01M 5/0058* (2013.01);
    (Continued)

(58) Field of Classification Search
    CPC ............. G01M 5/0025; G01M 5/0033; G01M 5/0058; G01N 3/08; G01N 2203/0017;
    (Continued)

(56) References Cited

U.S. PATENT DOCUMENTS

| | | |
|---|---|---|
| 3,854,328 A | 12/1974 | Schmidt |
| 2003/0154037 A1* | 8/2003 | Demia .................. G01L 1/2218 702/42 |

(Continued)

FOREIGN PATENT DOCUMENTS

| | | |
|---|---|---|
| JP | 2004-28976 A | 1/2004 |
| WO | 2003/096007 A1 | 11/2003 |
| WO | 2006/011484 A1 | 2/2006 |

OTHER PUBLICATIONS

Notification Concerning Transmittal of Translation of the International Preliminary Report on Patentability (Form PCT/IB/326) issued in counterpart International Application No. PCT/JP2015/070526 dated Feb. 9, 2017, with Forms PCT/IB/338, PCT/IB/373 and PCT/ISA/237. (13 pages).

(Continued)

*Primary Examiner* — Max H Noori
(74) *Attorney, Agent, or Firm* — Westerman, Hattori, Daniels & Adrian, LLP

(57) ABSTRACT

This internal pressure loading system includes an internal pressure loading device and an information processing device. The internal pressure loading device is set at an inner
(Continued)

face of a pipe, and includes a load meter which detects the load applied to the inner face of the pipe and a displacement meter which detects the deformation amount of the pipe. When the internal pressure loading device is expanded so as to increase the load to be detected by the load meter, the width of the pipe at which the displacement meter is located is reduced. On the basis of the load detected by the load meter and the deformation amount detected by the displacement meter, the information processing device evaluates the remaining strength of the pipe.

15 Claims, 14 Drawing Sheets

(52) U.S. Cl.
CPC ....... *G01N 3/08* (2013.01); *G01N 2203/0017* (2013.01); *G01N 2203/0062* (2013.01); *G01N 2203/0075* (2013.01); *G01N 2203/0218* (2013.01); *G01N 2203/0244* (2013.01); *G01N 2203/0274* (2013.01)

(58) Field of Classification Search
CPC ... G01N 2203/0062; G01N 2203/0075; G01N 2203/0218; G01N 2203/0244; G01N 2203/0274
USPC ........................................................... 73/789
See application file for complete search history.

(56) References Cited

U.S. PATENT DOCUMENTS

| | | | |
|---|---|---|---|
| 2005/0172697 A1 | 8/2005 | Nozaki et al. | |
| 2006/0217902 A1* | 9/2006 | Bernard | G01H 13/00 |
| | | | 702/47 |
| 2008/0134790 A1 | 6/2008 | Nozaki et al. | |
| 2008/0156123 A1 | 7/2008 | Nozaki et al. | |
| 2008/0314151 A1 | 12/2008 | Minagi et al. | |
| 2010/0212405 A1* | 8/2010 | Roberts | G01N 3/12 |
| | | | 73/49.6 |
| 2012/0143525 A1* | 6/2012 | Chen | G01L 1/246 |
| | | | 702/42 |
| 2014/0033825 A1* | 2/2014 | Ravet | G01B 11/18 |
| | | | 73/800 |
| 2017/0082526 A1* | 3/2017 | Kuroda | G01N 3/20 |

OTHER PUBLICATIONS

International Search Report dated Sep. 29, 2015, issued in counterpart International Application No. PCT/JP2015/070526 (1 page).

* cited by examiner

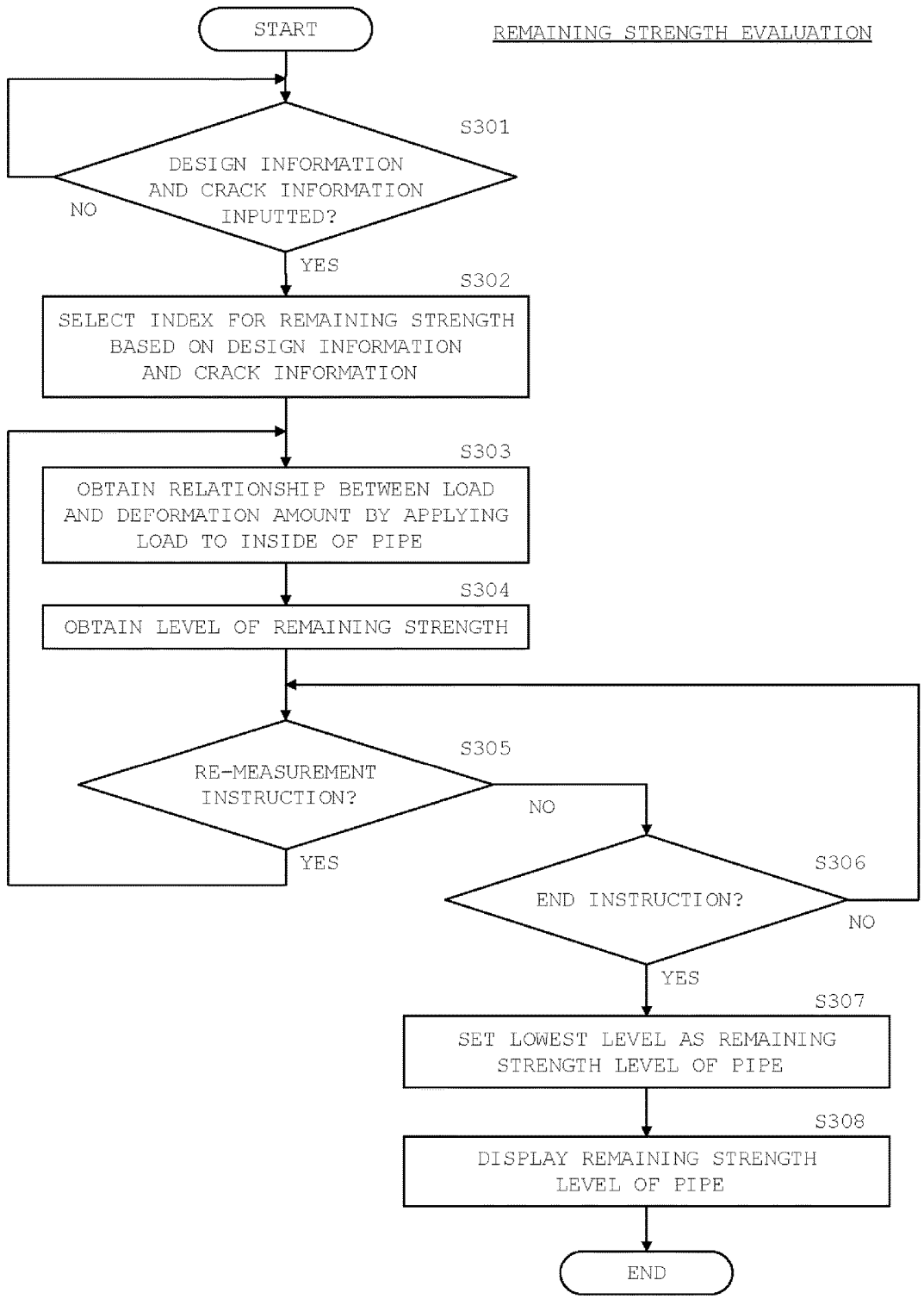

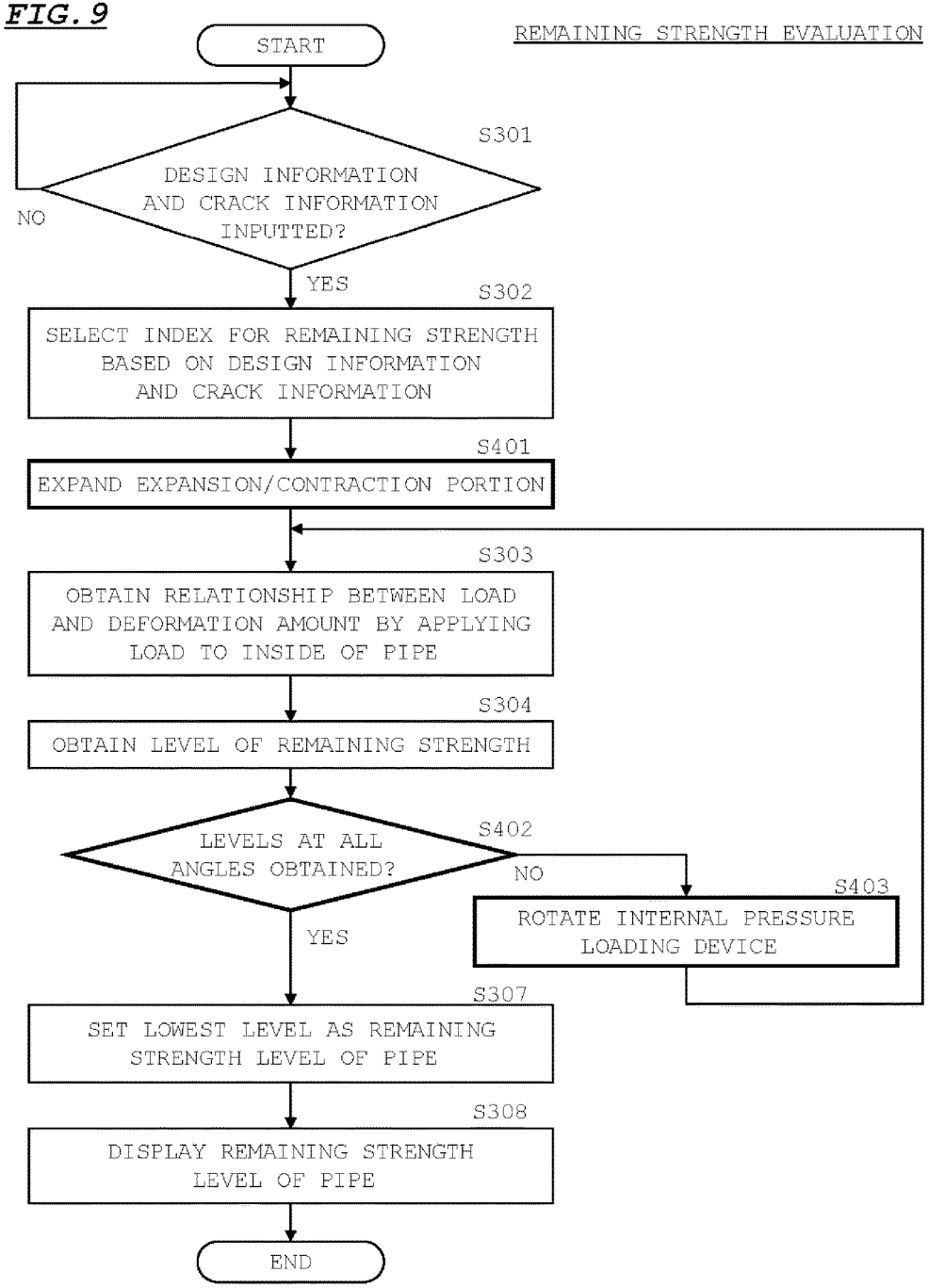

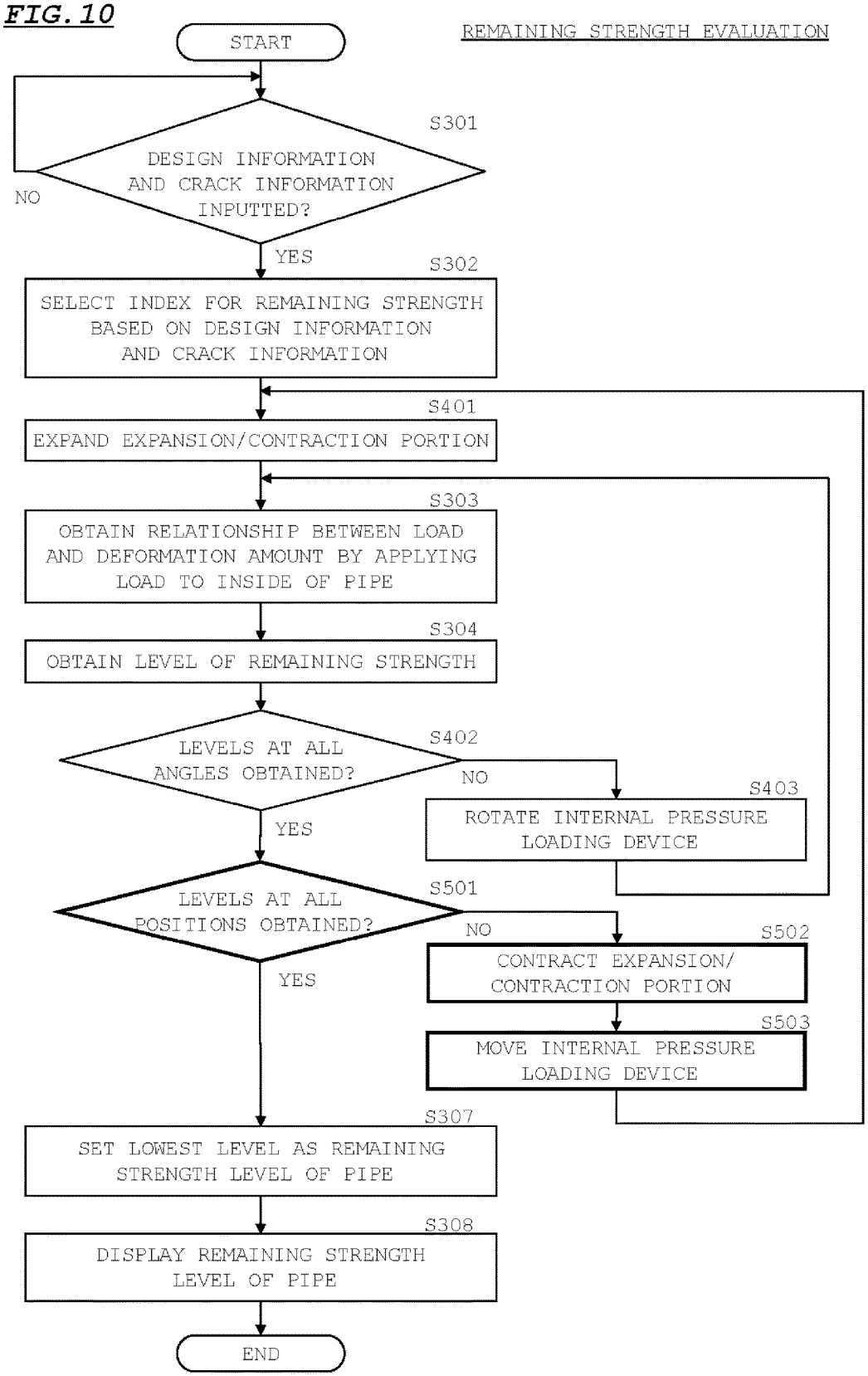

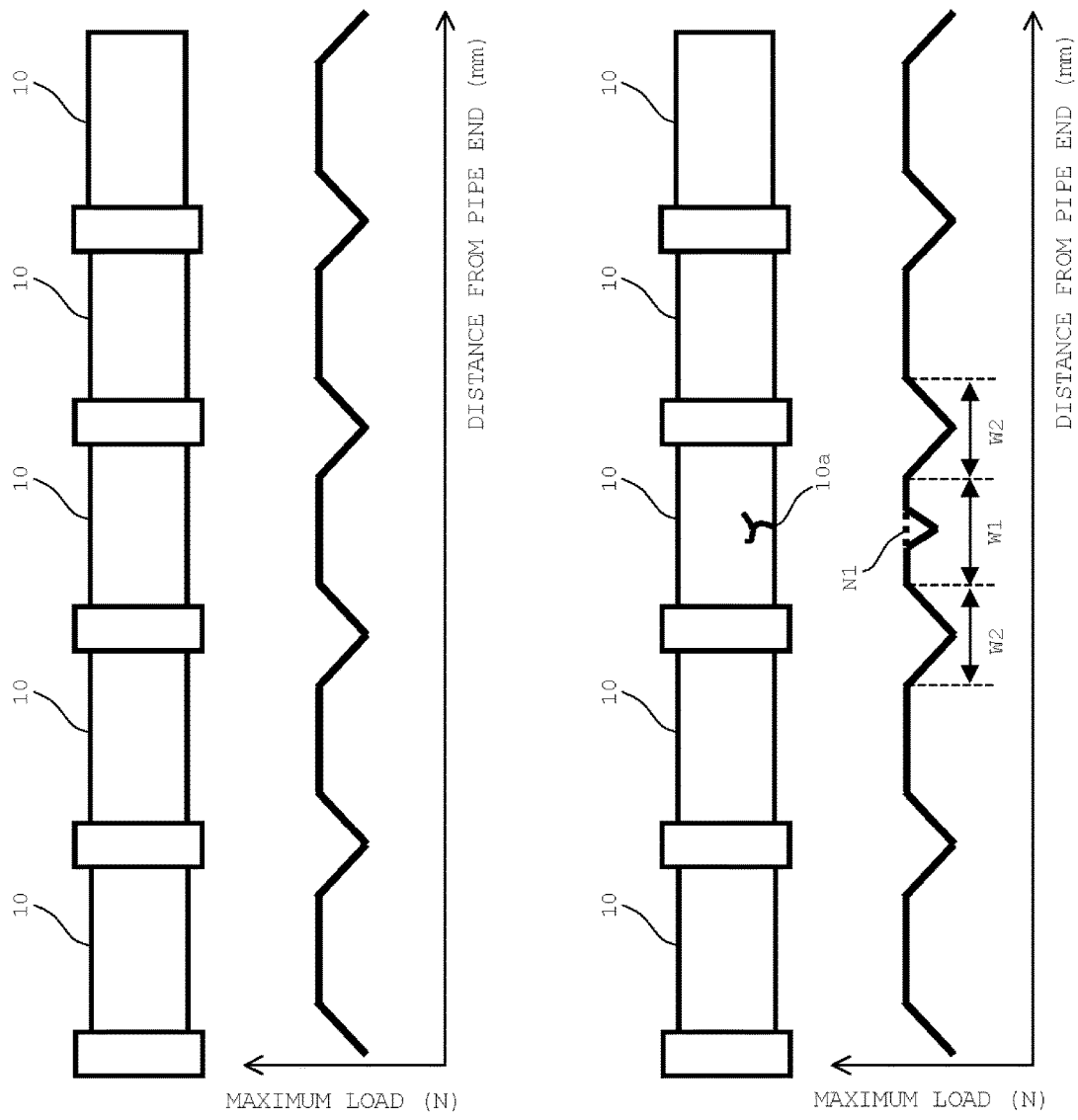

PIPE EVALUATION METHOD, MEASUREMENT DEVICE, AND PIPE EVALUATION SYSTEM

CROSS REFERENCE TO RELATED APPLICATION

This application is a continuation of International Application No. PCT/JP2015/070526 filed on Jul. 17, 2015, entitled "PIPE EVALUATION METHOD, MEASUREMENT DEVICE, AND PIPE EVALUATION SYSTEM", which claims priority under 35 U.S.C. Section 119 of Japanese Patent Application No. 2014-152382 filed on Jul. 25, 2014, entitled "PIPE EVALUATION METHOD, MEASUREMENT DEVICE, AND PIPE EVALUATION SYSTEM". The disclosure of the above applications is incorporated herein by reference.

BACKGROUND OF THE INVENTION

1. Field of the Invention

The present invention relates to an evaluation method for evaluating the remaining strength of an installed pipe, a measurement device to be used in the evaluation method, and a pipe evaluation system using the measurement device.

2. Disclosure of Related Art

Agricultural pipelines and sewerage pipelines that are laid underground include a large number of pipelines that have been laid underground for a long time. Such pipelines are often routed under roads and buildings, and thus, it is difficult to dig those pipes and lay new pipes. Therefore, in general, with respect to these pipelines, the remaining strength of the pipe is evaluated in a state where the pipe is buried in the soil, and then, the pipe is subjected to repair or reinforcement in accordance with the result of the evaluation. Japanese Laid-Open Patent Publication No. 2004-28976 describes a technique of evaluating the remaining strength of a pipe through an impact elastic wave test.

As mentioned above, the remaining strength of a pipe is usually evaluated in a state where the pipe is buried in the soil. However, with the technique described in Japanese Laid-Open Patent Publication No. 2004-28976, it is difficult to accurately evaluate the remaining strength of a pipe in a state where the pipe is buried in the soil, due to the influence of the ground surrounding the pipe. Therefore, conventionally, the state of the inside of the pipe is confirmed through visual observation to roughly evaluate the remaining strength of the pipe, and then, a construction method for repair and reinforcement is determined. Therefore, in order to ensure the safety, excessive repair or reinforcement of the pipe tends to be performed, thus causing problems such as increased cost and a prolonged construction period.

SUMMARY OF THE INVENTION

A first aspect of the present invention relates to an evaluation method for evaluating the remaining strength of a pipe. The pipe evaluation method according to the present aspect includes: applying a load to an inner face of the pipe in a first direction; detecting a deformation amount of the pipe in a second direction which is different from the first direction; and evaluating a remaining strength of the pipe on the basis of relationship between the load and the deformation amount.

A second aspect of the present invention relates to a measurement device to be set at an inner face of a pipe. The measurement device according to the present aspect includes: a pressurizing unit configured to apply a load to an inner face of the pipe in a first direction; and a detection unit configured to detect a deformation amount of the pipe in a second direction which is different from the first direction.

A third aspect of the present invention relates to an evaluation system for evaluating the remaining strength of a pipe. The pipe evaluation system according to the present aspect includes: a measurement device according to the second aspect, and an information processing unit. The information processing unit evaluates the remaining strength of the pipe on the basis of relationship between the load and the deformation amount.

BRIEF DESCRIPTION OF THE DRAWINGS

The above and other objects and new features of the present invention will be fully clarified by the following description of the embodiment, when read in conjunction with accompanying drawings.

FIG. 7 is a flow chart showing a procedure of remaining strength evaluation performed when an internal pressure loading system according to the embodiment is used;

FIG. 9 is a flow chart showing a procedure of the remaining strength evaluation performed when the internal pressure loading system according to Modification 1 is used;

FIG. 10 is a flow chart showing a procedure of the remaining strength evaluation performed when the internal pressure loading system according to Modification 2 is used;

FIG. 12A shows how the maximum load of each pipe varies when pipes are coupled together according to Modification 3;

FIG. 12B shows how the maximum load of each pipe varies when a crack has occurred in one pipe, in a case where pipes are coupled together;

It should be noted that the drawings are solely for description and do not limit the scope of the present invention.

DESCRIPTION OF THE PREFERRED EMBODIMENTS

1. Remaining Strength Evaluation Method

First, a remaining strength evaluation method performed on a pipe buried in the soil (installed pipe) will be described.

Here, the remaining strength means the strength that remains in the pipe, and represents how much the pipe can bear a load. The greater the remaining strength is, the greater the limit load is that the pipe can bear without being crushed.

Figure 1A:
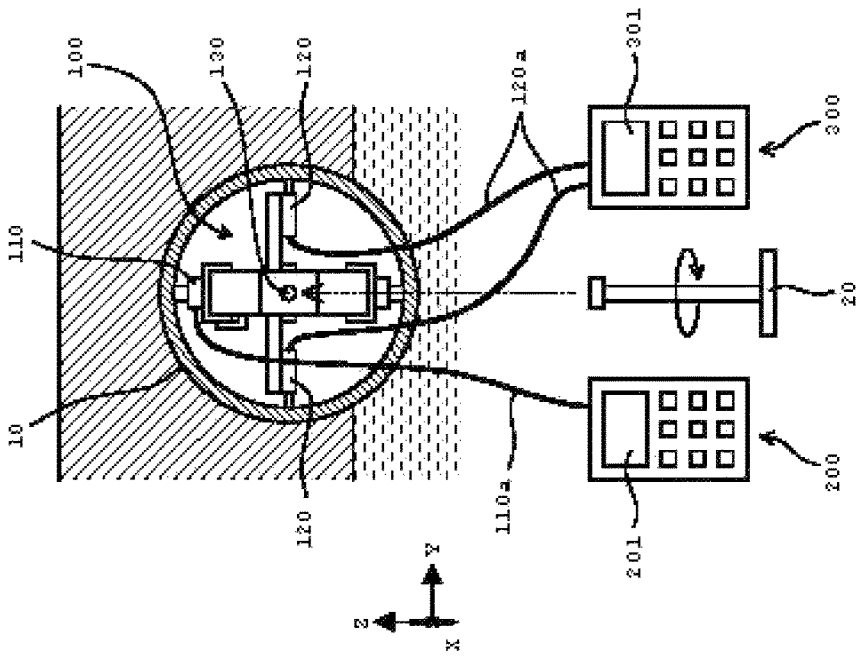
FIG. 1A shows an operation flow before evaluation of the remaining strength of an installed pipe is performed according to an embodiment.
Figure 1B:
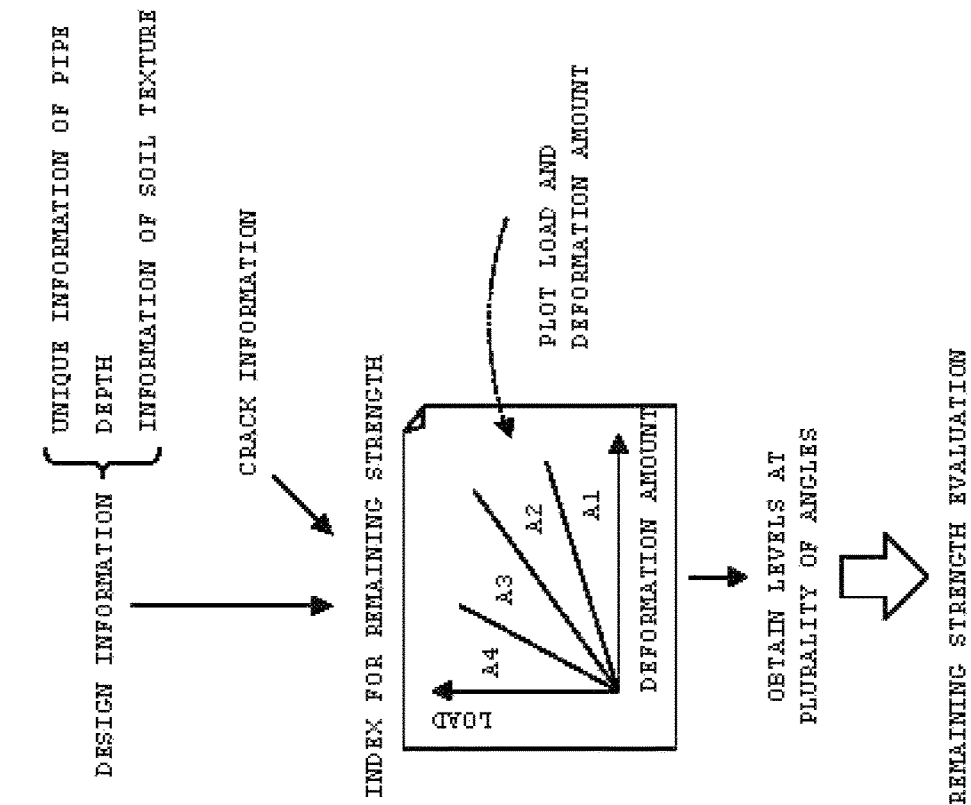
FIG. 1B is a schematic diagram showing a configuration for obtaining the relationship between the load and the deformation amount from the installed pipe.

FIG. 1A shows an operation flow before evaluation of the remaining strength of an installed pipe is performed. FIG. 1B is a schematic diagram showing a configuration for obtaining the relationship between the load and the deformation amount from the installed pipe. The remaining strength evaluation is performed in a state where the pipe as an evaluation target is buried in the soil.

With reference to FIG. 1A, in an evaluation method of the present embodiment (internal pressure loading method), a load in one direction is applied to the inner side of an installed pipe, and on the basis of the deformation amount of the pipe at this time, the remaining strength of the installed pipe is evaluated. Prior to evaluation of the remaining strength, an index for evaluating the remaining strength is prepared in advance. This index is prepared for each combination of design information of the pipe and crack information indicating the characteristic of the pipe.

Here, the design information is a matter contained in the drawings and specifications. The design information includes: unique information of the pipe; depth from the ground surface to the pipe; and information of the texture of the soil (soil texture) in which the pipe is buried. The unique information of the pipe includes: the kind of the pipe (for example, reinforced concrete pipe, vinyl chloride pipe, reinforced plastic composite pipe, ductile cast iron pipe, etc.); inner diameter of the pipe; outer diameter of the pipe; and the like. The information of the soil texture includes: weight per unit volume of the soil; internal friction angle of the soil; support angle; reaction force coefficient of the base material; and the like. The crack information includes the position of the crack (up, down, left, right, etc.), the number of cracks, and the like.

When a load is applied to the inner side of a pipe to push the pipe in one direction, the pipe is contracted in a direction that crosses this direction. The deformation amount at this time differs depending on the remaining strength of the pipe, i.e., the strength that remains in the pipe. In addition, this deformation amount varies also depending on the properties unique to the pipe itself (unique information), the characteristic of the pipe (state of crack), and the environment surrounding the pipe (depth at which the pipe is buried, soil texture around the pipe). The deeper the depth at which the pipe is buried, the greater the pressure applied to the pipe is, and thus, the pipe is less likely to be deformed. The harder the soil texture around the pipe is, the less likely the pipe is deformed. Taking these matters into consideration, an index for evaluating the remaining strength of the pipe is prepared for each combination of the design information of the pipe and the crack information indicating the characteristic of the pipe.

Each index includes: a graph whose two axes respectively represent the load applied to the inner side of a pipe, and the deformation amount of the pipe; and regions A1 to A4 respectively corresponding to levels 1 to 4 of the remaining strength set on this graph. Here, levels 1 to 4 represent the magnitudes of the remaining strength in this order. At Level 1, the remaining strength is lowest, and at level 4, the remaining strength is highest. Level 1 represents a state where the pipe cannot be renovated. Level 2 represents a state where repair or reinforcement by use of a self-supporting pipe is required in the case of a pipe rehabilitation technique, for example. Level 3 represents a state where repair or reinforcement by use of a double-layer pipe or a composite pipe is required in the case of a pipe rehabilitation technique, for example. Level 4 represents a state where there is no problem in continuous use of the pipe.

These indexes are created through theoretical simulation (arithmetic processing using analytical software) in which the design information and the crack information are used as parameters. Alternatively, in such a case where a pipe is dug out and a new pipe is to be laid, an index is created by actually measuring the pipe having been installed, and then, the created index replaces an index created through simulation. A method for creating indexes through actual measurement will be described later with reference to FIG. 4.

In the remaining strength evaluation, the relationship between the load and the deformation amount of the pipe as an evaluation target is obtained. Then, a remaining strength level is obtained, on the basis of which region (region A1 to A4) on the graph of the index corresponding to the design information and the crack information of the pipe includes plotted points corresponding to the obtained relationship between the load and the deformation amount.

The deformation amount of the pipe is obtained by the configuration shown in FIG. 1B. As shown in FIG. 1B, in a state where a pipe 10 as an evaluation target is buried in the soil, a measurement device for obtaining the relationship between the load and the deformation amount (hereinafter, referred to as "internal pressure loading device") is set inside the pipe 10. In FIG. 1B, XYZ coordinate axes which are orthogonal to one another are shown for convenience. The X-axis direction represents the longitudinal direction of the pipe 10, and the Z-axis positive direction represents the vertical and upward direction.

An internal pressure loading device 100 includes a load meter 110, two displacement meters 120, and a rotation portion 130. The load meter 110 is connected to a load measuring unit 200 via a cable 110*a*, and each displacement meter 120 is connected to a displacement measuring unit 300 via a cable 120*a*. The internal pressure loading device 100 has a configuration similar to that of a jack, and the rotation portion 130 serves as a power input portion for the jack. When the rotation portion 130 is rotated, the internal pressure loading device 100 expands/contracts in the up-down direction.

Figure 2:
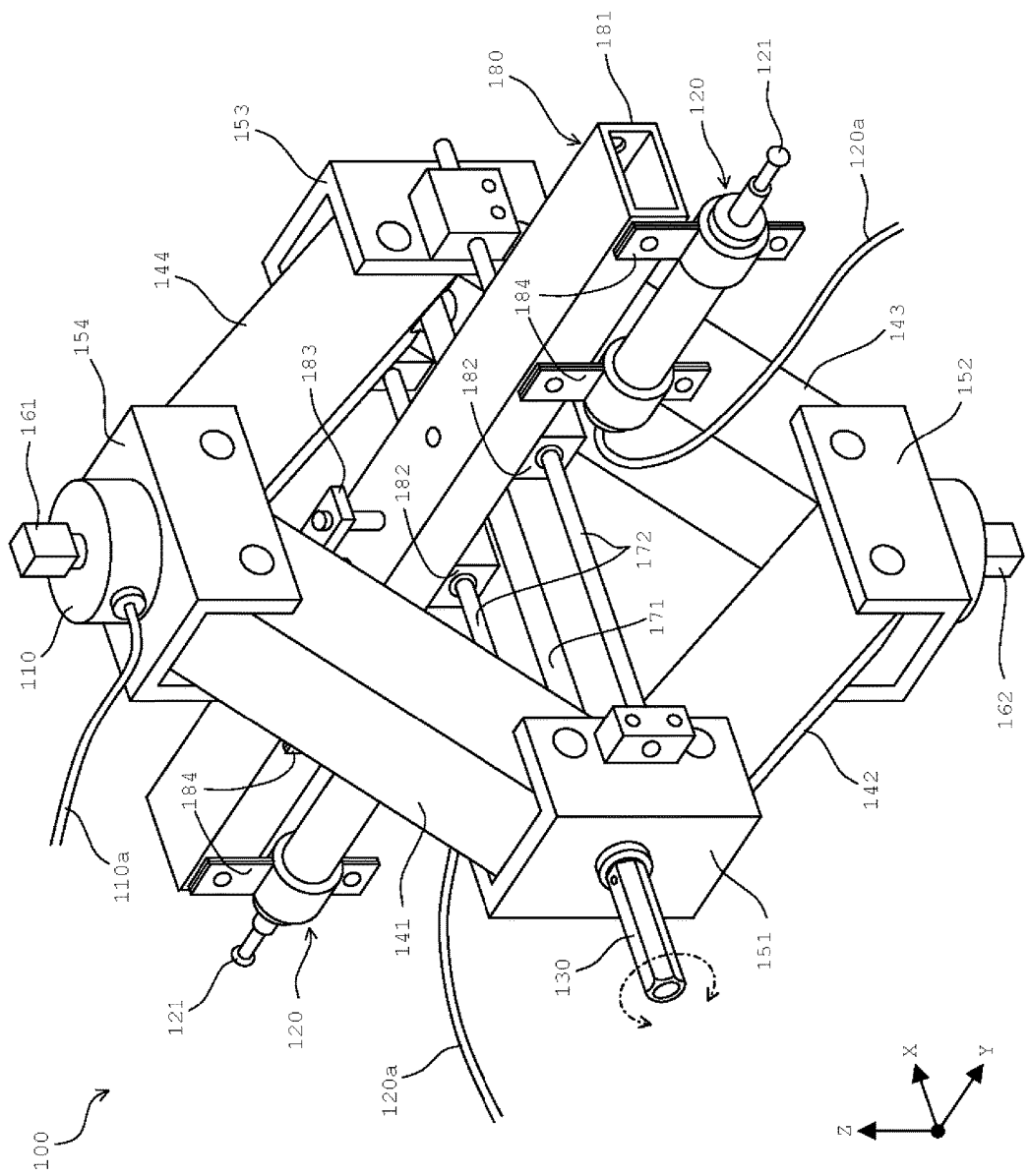
FIG. 2 shows a configuration of an internal pressure loading device according to the embodiment.

FIG. 2 shows a configuration of the internal pressure loading device 100. The X, Y, and Z axes shown in FIG. 2 correspond to the X, Y, and Z axes shown in FIG. 1B, respectively.

The internal pressure loading device 100 includes frame members 141 to 144, support members 151 to 154, grounding members 161, 162, a long screw 171, two bars 172, and a support body 180, in addition to the load meter 110, the displacement meters 120, and the rotation portion 130 described above.

The frame members 141 and 142 are rotatably joined to each other, the frame members 142 and 143 are rotatably joined to each other, the frame members 143 and 144 are rotatably joined to each other, and the frame members 144 and 141 are rotatably joined to each other, by the support members 151 to 154, correspondingly. As a result, the outline of the structure formed by the frame members 141 to 144 is in a rhombic shape. This allows the internal pressure loading device 100 to expand/contract in the Z-axis direction.

The load meter 110 is set on the upper face of the support member 154. The grounding member 161 is set above the load meter 110. The load meter 110 detects a load by the grounding member 161 being pushed into the Z-axis negative direction. The grounding member 162 is set on the lower face of the support member 152. The distance from the upper face of the grounding member 161 to the upper face of the support member 154 is equal to the distance from the lower face of the grounding member 162 to the lower face of the support member 152.

The long screw 171 has a thread groove formed therein, and end portions in the X-axis direction of the long screw 171 are supported in screw holes (not shown) formed in faces, of the support members 151 and 153, that are parallel to the Y-Z plane. In the inner faces of the screw holes formed in the support members 151 and 153, thread grooves in opposite directions are formed, respectively. When viewed in the Y-axis direction, the position of the long screw 171 matches the diagonal line in the X-axis direction of the rhombic shape formed by the frame members 141 to 144. The end portion on the X-axis negative side of the long screw 171 protrudes from a side face on the X-axis negative side of the support member 151, and the rotation portion 130 is fixed to this protruding portion. When the rotation portion 130 is rotated about the X-axis with a wrench 20 (see FIG. 1B), the long screw 171 is rotated about the X-axis, whereby the distance between the support member 151 and the support member 153 is changed. Accordingly, the structure having the rhombic shape and formed by the frame members 141 to 144 expands/contracts in the Z-axis direction, whereby the internal pressure loading device 100 expands/contracts in the Z-axis direction.

End portions of the bar 172 on the Y-axis positive side are fixed to side faces on the Y-axis positive side of the support members 151 and 153, respectively. End portions of the bar 172 on the Y-axis negative side are fixed to end portions on the Y-axis negative side of the support members 151 and 153, respectively. The two bars 172 are parallel to the X-axis direction.

The support body 180 includes: a support member 181 extending in the Y-axis direction; two slide portions 182 provided at the lower face of the support member 181; and a fixture 183 provided at the upper face of the support member 181; and four fixtures 184 provided at the side face on the X-axis negative side of the support member 181. Each slide portion 182 has a hole formed therein that penetrates the slide portion 182 in the X-axis direction. The bar 172 is passed through this hole. Accordingly, the support body 180 can slide in the X-axis direction relative to the two bars 172. The fixture 183 connects the upper face of the support member 181 to a side face on the Y-axis negative side of the support member 154. Accordingly, when viewed in the Z-axis direction, the position of the support member 181 relative to the support member 154 is always constant.

The displacement meter 120 on the Y-axis positive side includes a displacement portion 121 at the end on the Y-axis positive side thereof. The displacement meter 120 on the Y-axis negative side includes a displacement portion 121 at the end on the Y-axis negative side thereof. Each of the two displacement meters 120 is fixed to the support member 181 by two fixtures 184. When viewed in the Y-axis direction, the position of the two displacement portions 121 matches the intersection of the diagonal lines of the rhombic shape formed by the frame member 141 to 144. When viewed in the Z-axis direction, the two displacement portions 121 are at positions symmetric to each other relative to the long screw 171. When each displacement portion 121 is pushed toward the center of the internal pressure loading device 100, the corresponding displacement meter 120 detects a deformation amount that corresponds to the pushed amount.

When the internal pressure loading device 100 is configured as described above and set as shown in FIG. 1B, the positions in the Z-axis direction of the two displacement portions 121 are aligned with the center position of the pipe. In addition, the positions in the X-axis direction of the two displacement portions 121 are at the inner face of the pipe to which a load is applied. Thus, deformation of the pipe caused by the load can be accurately measured.

Figure 3:
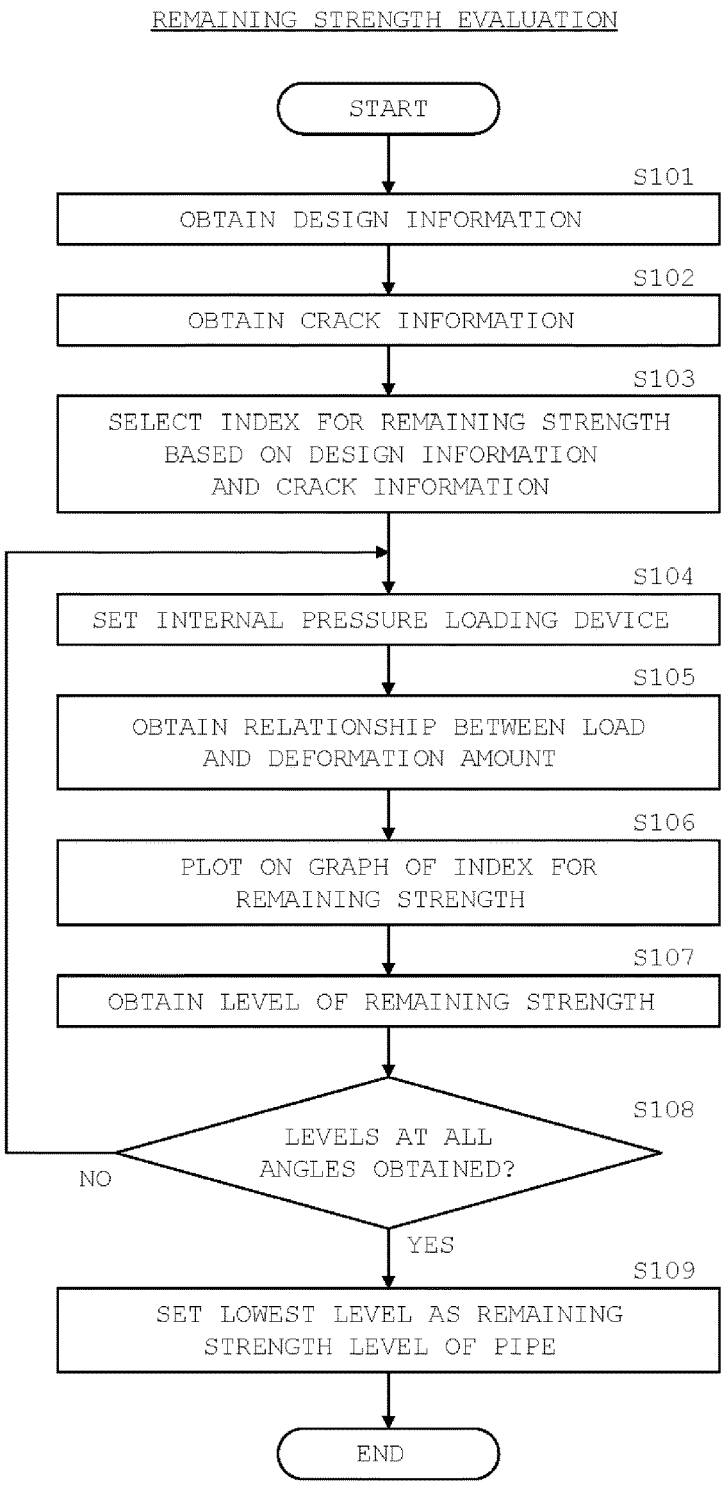
FIG. 3 is a flow chart showing a procedure of remaining strength evaluation according to the embodiment.

FIG. 3 is a flow chart showing a procedure of the remaining strength evaluation.

An operator refers to the drawings and specifications to obtain design information regarding a pipe as an evaluation target, (S101), and visually observes the pipe as an evaluation target from inner side thereof to obtain crack information of the pipe (S102). Subsequently, the operator selects an index for remaining strength to be used in the remaining strength evaluation, on the basis of the obtained design information and crack information (S103). Indexes for remaining strength are categorized according to the combinations of design information and crack information. The operator selects, as the index to be used in the evaluation of the pipe as an evaluation target, an index that is most appropriate for the design information and the crack information of the pipe as an evaluation target.

Since which pipe is to be laid at the time of laying is determined mainly on the basis of flow rate and water pressure, the design information may include "flow rate and water pressure" instead of the unique information of the pipe.

Next, the operator sets the internal pressure loading device 100 such that the direction in which to apply a load is aligned with the vertical direction as described with reference to FIG. 1B (S104), and obtains the relationship between the load and the deformation amount from the pipe as an evaluation target (S105). It should be noted that the deformation amount may be a sum of values obtained from the two displacement portions 121, or may be a value obtained from one displacement portion 121. In a case where the value obtained from one displacement portion 121 is used as the deformation amount, the other displacement portion 121 is used in determining whether the internal pressure loading device 100 is appropriately set in the pipe, for example.

In S105, a plurality of deformation amounts are obtained with the load changed. As shown in FIG. 1B, the operator rotates the rotation portion 130 with the wrench 20 to expand the internal pressure loading device 100 in the up-down direction, thereby to apply a load in the up-down direction to the inner face of the pipe 10 and widen the width in the up-down direction of the pipe 10. The operator refers to a display part 201 of the load measuring unit 200 to obtain the load applied in the up-down direction 10 from the inner side of the pipe by the internal pressure loading device 100, and refers to a display part 301 of the displacement measuring unit 300 to obtain the deformation amount in the horizontal direction of the pipe 10. Further, the operator rotates the wrench 20 such that the load is gradually increased, and obtains deformation amounts at a plurality of different loads, respectively.

Subsequently, the operator plots the obtained relationship between the load and the deformation amount, on a graph of the index for remaining strength obtained in S103 (S106), and obtains the level of the remaining strength of the pipe on the basis of the plotted dots (S107).

In a case where the plotted dots are included in a plurality of regions, the level of the region that includes the greatest number of plotted dots is obtained as the remaining strength level. If there are a plurality of regions that each includes the greatest number of plotted dots, i.e., for example, if two regions includes the same number of plotted dots, the lowest level among the levels of such regions is obtained as the remaining strength level. The remaining strength level may be obtained by another method. For example, the plotted dots are connected by a line, then, it is determined which region includes the intersection of this line and a straight line that indicates a predetermined load and that is parallel to the horizontal axis, and on the basis of this determination, the remaining strength level may be obtained.

Next, the operator rotates the internal pressure loading device 100 by a predetermined angle about the X-axis, and repeats the operations of S104 to S107. When the operator has obtained levels of remaining strength at all angles (S108: YES), then, among the obtained levels of remaining strength at the plurality of angles, the lowest level of remaining strength is set as the level of remaining strength of this pipe (S109). Thus, the remaining strength evaluation for the pipe ends.

In S109, among the obtained levels of remaining strength, the lowest level is set as the level of remaining strength of the pipe. However, in such a case where the number of lowest levels of remaining strength is one, the level of remaining strength may be determined on the basis of the significance of the pipe as an evaluation target (for example, whether the pipe is buried in a residential area, in a farm land, or the like).

Figure 4:
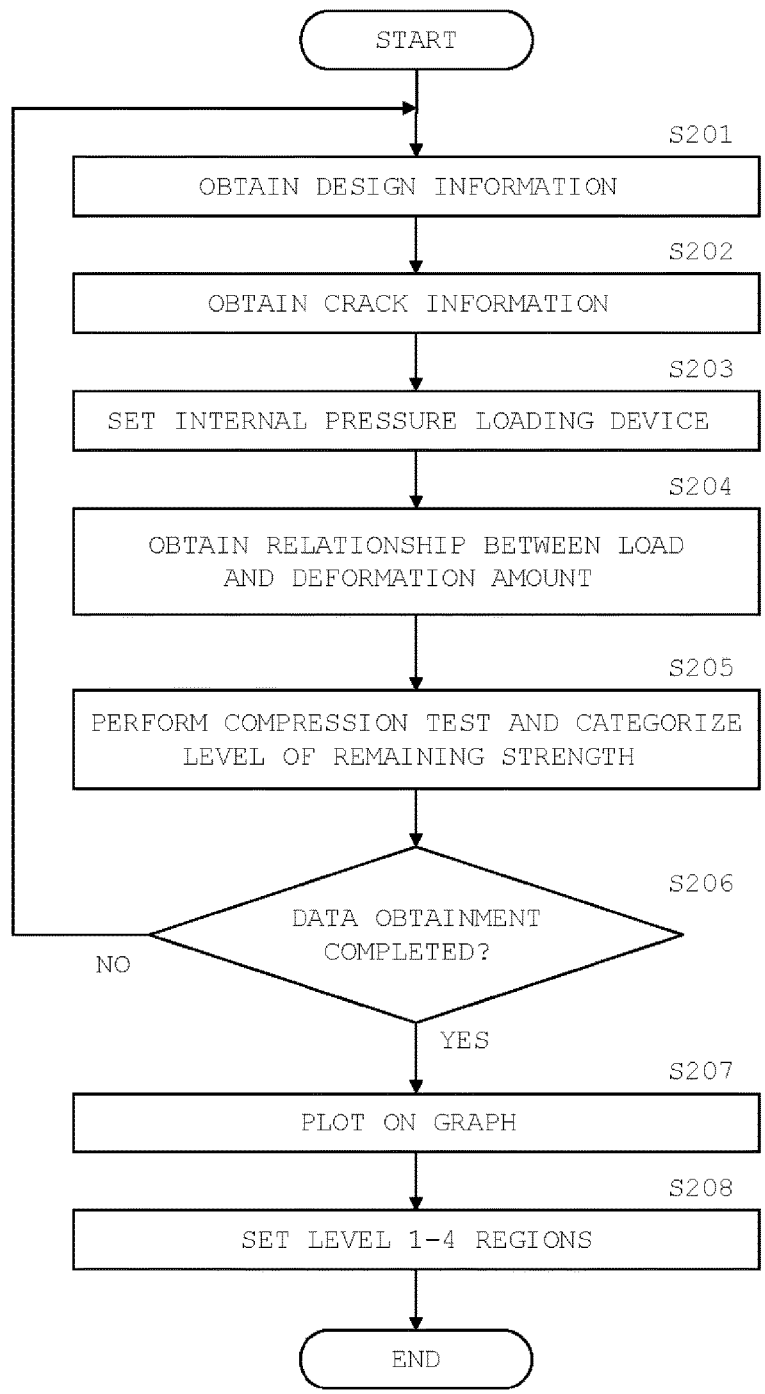
FIG. 4 is a flow chart showing a procedure of creating an index for remaining strength through actual measurement according to the embodiment.

FIG. 4 is a flow chart showing a procedure of creating an index for remaining strength through actual measurement. Creation of an index according to this procedure is performed through actual measurement of an installed pipe, in such a case where a pipe is dug out and a new pipe is to be laid.

The operator refers to the drawings and specifications to obtain design information regarding a target installed pipe (S201), and visually observes, from inner side, the installed pipe before being dug out, and obtains crack information of the pipe (S202). Subsequently, the operator sets the internal pressure loading device 100 in the installed pipe before being dug out such that the direction in which to apply a load is aligned with the vertical direction as described with reference to FIG. 1B (S203). Then, the operator obtains the relationship between the load and the deformation amount from this pipe (S204). Subsequently, the operator causes this pipe to be taken out of the soil, performs a compression test to measure the load at which the pipe is broken, and on the basis of this measured value, categorizes the level of remaining strength of this pipe into one of levels 1 to 4 (S205). Thus, if the pipe is taken out of the soil and is actually subjected to a compression test in this manner, the level of remaining strength of the pipe can be accurately ascertained.

Figure 5A:
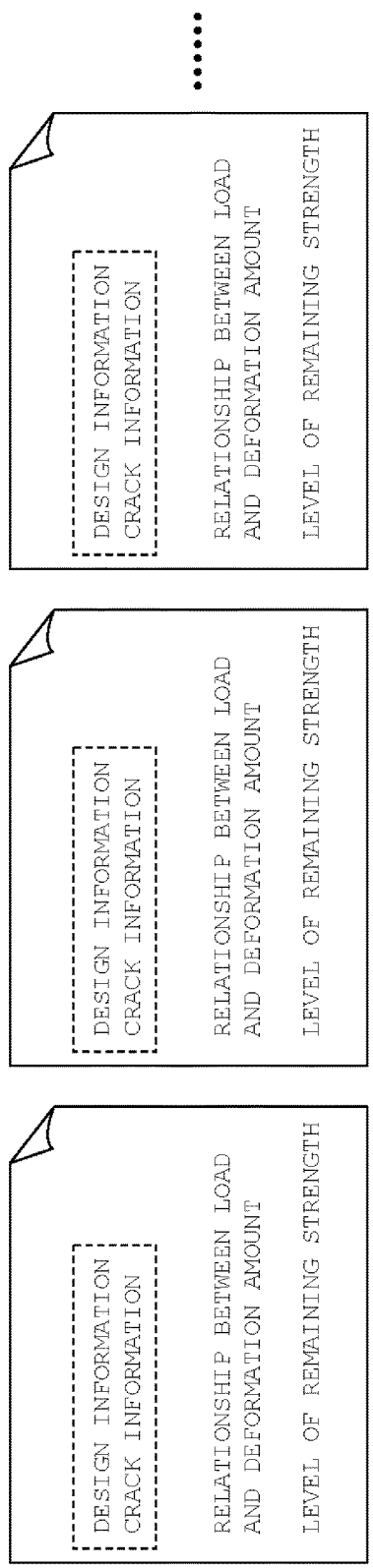
FIG. 5A illustrates a concept of how the relationship between the load and the deformation amount and the level of the remaining strength are obtained according to the embodiment.

Next, the operator performs the procedure of S201 to S205 also with respect to other pipes that have design information and crack information that match those of the above pipe. Accordingly, as shown in FIG. 5A, with respect to each of a plurality of pipes that have the same design information and crack information, a relationship between the load and the deformation amount and a level of remaining strength are obtained.

Figure 5B:
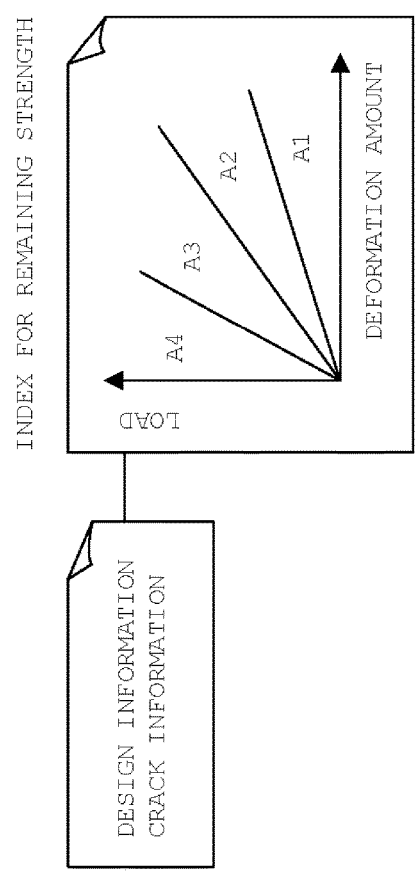
FIG. 5B illustrates a concept of how an index for remaining strength is created so as to be associated with design information and crack information according to the embodiment.

Next, with respect to the pipes that have the same design information and crack information, when relationships between the load and the deformation amount and levels of remaining strength have been sufficiently obtained (S206: YES), the operator plots, on a graph whose two axes represent the load and the deformation amount, the relationship between the load and the deformation amount obtained for each of the plurality of installed pipes (S207). Subsequently, on the created graph, the operator sets distribution regions of plotted dots having the levels of remaining strength of 1 to 4, into regions A1 to A4, respectively (S208). The regions A1 to A4 are obtained by setting boundaries between regions where plotted dots of levels 1 to 4 are distributed, respectively. Accordingly, as shown in FIG. 5B, an index for remaining strength is created that is associated with design information and crack information. Other indexes for remaining strength regarding different design information and crack information can be obtained by the process shown in FIG. 4 being performed on other installed pipes having different design information and crack information.

In FIG. 1A and FIG. 5B, the boundaries on the graph included in the index for remaining strength are in the form of straight lines. However, depending on design information and crack information, the boundaries are not necessarily realized in the form of straight lines in some cases. In addition, here, the number of regions set on the graph is four, but may not necessarily be four, and can be changed as appropriate in accordance with how much repair or reinforcement is to be made. In order to assure reliable repair or reinforcement, after the index for remaining strength has been created as described above, the boundaries between the regions may be shifted by a predetermined width toward the higher level side, i.e., toward the higher remaining strength side. This makes the remaining strength more likely to be evaluated as low, and thus, repair or reinforcement can be further assuredly performed.

Creation of an index for remaining strength by the procedure shown in FIG. 4 requires actual measurements and compression tests to be performed on a large number of installed pipes. Thus, it is difficult to create an index for remaining strength through actual measurement for each of all combinations of design information and crack information. Therefore, preferably, indexes for remaining strength are initially created and prepared through simulation using analytical software; and then, with respect to design information with which laying is often performed, indexes are created as necessary through actual measurement, and the indexes created through simulation are replaced with the indexes created through actual measurement.

According to the remaining strength evaluation method described above, in a state where the pipe as an evaluation target is buried in the soil, the internal pressure loading device 100 applies a load to the inner face of the pipe, and detects the deformation amount of the inner face of the pipe. In this case, the relationship between the load and the deformation amount is obtained, with influence of the surrounding ground included. Therefore, on the basis of the obtained relationship between the load and the deformation amount, it is possible to appropriate evaluate the remaining strength of the pipe in a state where the pipe is buried in the soil. In addition, since only the necessary repair or reinforcement can be performed, excessive repair or reinforcement can be suppressed from being performed, and increase in cost and prolongation of the construction period can be suppressed.

According to the remaining strength evaluation method described above, an index for remaining strength is selected on the basis of design information and crack information. Then, on the basis of the selected index for remaining strength and the obtained relationship of the load and the deformation amount, remaining strength evaluation of the installed pipe is performed. Accordingly, the remaining strength of the pipe can be easily and appropriately evaluated.

According to the remaining strength evaluation method described above, crack information of the pipe is used as an indicator of the characteristic of the pipe, and the depth at which the pipe is buried and the soil texture around the pipe are used as a burying condition. A deformation amount of a pipe changes depending on crack information, and also changes depending on the depth at which the pipe is buried (pressure applied on the pipe) and on the soil texture around the pipe (softness of the soil around the pipe). Therefore, by configuring the index for evaluation on the basis of these elements, it is possible to accurately evaluate the remaining strength of the pipe.

According to the remaining strength evaluation method described above, the angle between the direction in which to apply a load to the inner side of the pipe, and the direction in which to detect deformation of the pipe by the displacement meter 120, is 90 degrees. Accordingly, the deformation amount of the portion where the greatest deformation occurs upon application of a load can be detected.

According to the remaining strength evaluation method described above, the level of remaining strength is obtained at a plurality of angles by rotating the internal pressure loading device 100 in the circumferential direction, and the lowest level of remaining strength is set as the level of the remaining strength of this pipe. Thus, since the remaining strength of the pipe is searched for in the circumferential direction of the pipe, the remaining strength of the pipe can be more appropriately evaluated.

According to the remaining strength evaluation method described above, simply by setting the internal pressure loading device 100 inside an installed pipe and rotating the wrench 20, it is possible to obtain the relationship between the load and the deformation amount. Accordingly, it is not necessary to prepare a big device at the site where the pipe as an evaluation target is buried, and it is possible perform remaining strength evaluation through simple operation of performing the procedure shown in FIG. 1A by use of the internal pressure loading device 100.

According to the remaining strength evaluation method described above, prior to actual evaluation, the relationships between the load and the deformation amount are detected from other pipes in a state of being buried in the soil. Then, the remaining strengths of the other pipes are evaluated through compression tests. Then, on the basis of the relationships between the load and the deformation amount of the other pipes and the results of evaluation of the remaining strength of the other pipes, an index for remaining strength is created. In this manner, since the index is set on the basis of actual measurement, accuracy of the index is increased. Accordingly, accuracy of the remaining strength evaluation in actual evaluation can be increased.

2. Internal Pressure Loading System

When evaluating the remaining strength of an installed pipe by the procedure described above, the operator needs to select an index for remaining strength to be used in the evaluation, on the basis of design information and crack information, and then, needs to plot loads and deformation amounts on a graph, thereby determining the level of the remaining strength. Such operation is preferably performed automatically, not by the operator. Hereinafter, an internal pressure loading system will be described that allows automatic evaluation of the remaining strength of an installed pipe.

An internal pressure loading system 1 described below corresponds to "pipe evaluation system" described in claims. The internal pressure loading device 100 corresponds to "measurement device" described in claims. The displacement meter 120 corresponds to "detection unit" described in claims. The frame members 141 to 144 and the long screw 171 correspond to "pressurizing unit" described in claims. An information processing device 400 corresponds to "information processing unit" described in claims.

Figure 6:
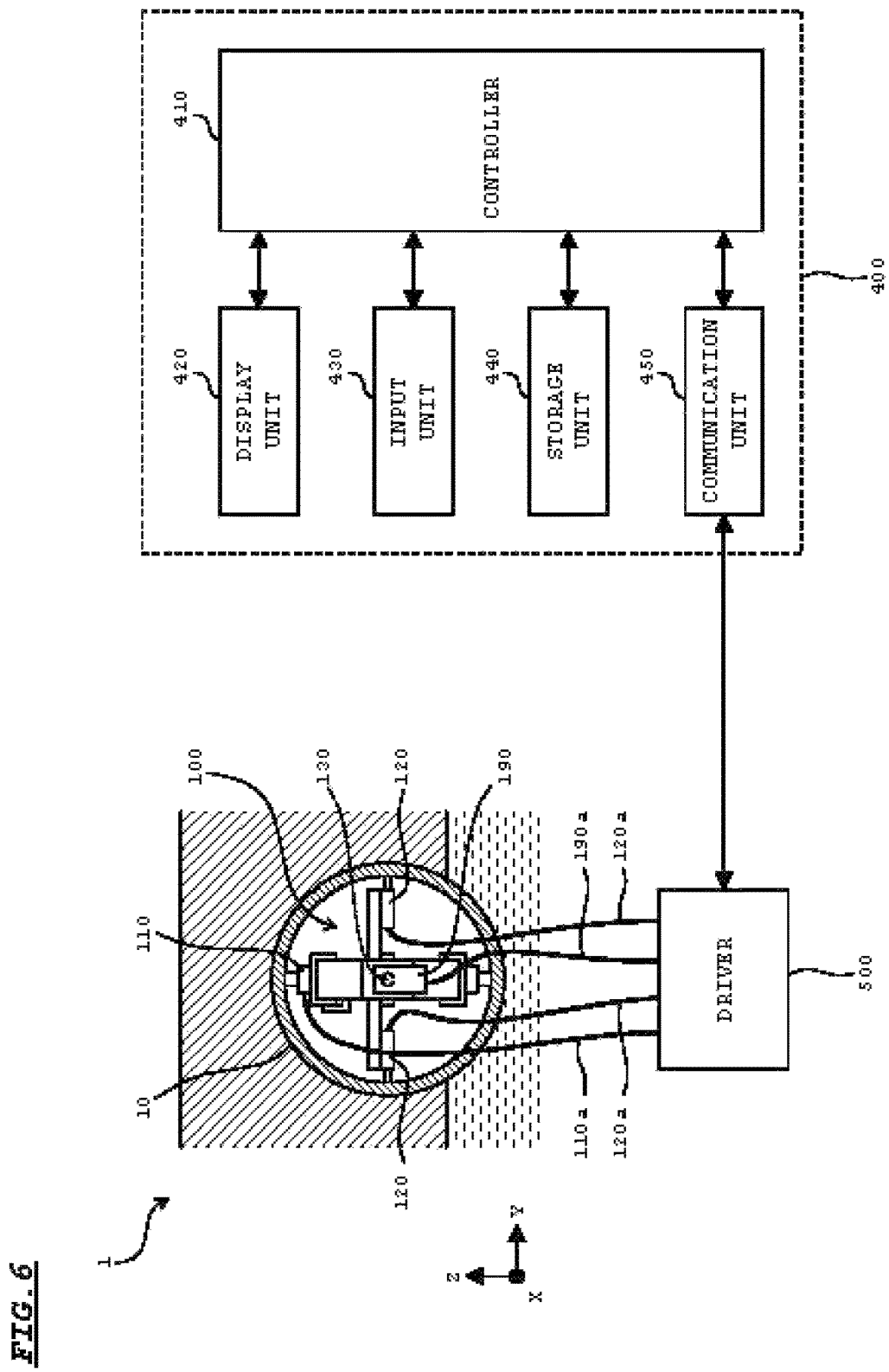
FIG. 6 is a schematic diagram showing a configuration of an internal pressure loading system according to the embodiment.

FIG. 6 is a schematic diagram showing a configuration of the internal pressure loading system 1.

The internal pressure loading system 1 includes: the internal pressure loading device 100; the information processing device 400, and a driver 500. The internal pressure loading device 100 shown in FIG. 6 additionally includes a motor 190, compared with the internal pressure loading device 100 shown in FIG. 1B. The motor 190 is connected to the driver 500 via a cable 190a, and is supplied with a drive current from the driver 500. The load meter 110 and the displacement meters 120 are connected to the driver 500 via the cables 110a, 120a, respectively, and a load and a displacement are detected by the driver 500.

The information processing device 400 is a personal computer or the like, and includes a controller 410, a display unit 420, an input unit 430, a storage unit 440, and a communication unit 450. The controller 410 controls the components of the information processing device 400, and performs processing such as calculation, etc. on the basis of computer programs stored in the storage unit 440. In the storage unit 440, a plurality of indexes for remaining strength are stored, categorized according to design information and crack information. The controller 410 performs transmission/reception of signals to/from the driver 500 via the communication unit 450. The display unit 420 is composed of a display, and the input unit 430 is composed of a keyboard and/or a mouse. The display unit 420 and the input unit 430 may be integrally formed as a touch panel display, or the like.

FIG. 7 is a flow chart showing a procedure of the remaining strength evaluation performed when the internal pressure loading system 1 is used.

First, the operator sets the internal pressure loading device 100 in an installed pipe as an evaluation target, and inputs design information and crack information via the input unit 430. When the design information and the crack information have been inputted (S301: YES), the controller 410 selects an index for remaining strength that corresponds to the inputted design information and crack information, from among the plurality of indexes for remaining strength which are stored in the storage unit 440 in advance (S302).

Subsequently, the controller 410 drives the motor 190 to rotate the rotation portion 130, thereby to apply a load to the inside of the pipe 10. At this time, the controller 410 drives the motor 190 on the basis of the design information such that an appropriate load is applied to the inside of the pipe. In addition, the controller 410 receives signals from the load meter 110 and the displacement meter 120. Then, the controller 410 obtains deformation amounts at plurality of different loads while driving the motor 190 such that the load is gradually increased, and thereby obtains the relationship between the load and the deformation amount (S303). Subsequently, the controller 410 obtains a level of the remaining strength of the pipe, on the basis of the index for remaining strength selected in S302 and the relationship between the load and the deformation amount obtained in S303 (S304).

Next, the controller 410 drives the motor 190 such that the load of the load meter 110 becomes 0, and waits for an input from the operator. The operator changes the setting angle of the internal pressure loading device 100, and inputs a re-measurement instruction via the input unit 430. When the re-measurement instruction has been inputted (S305: YES), the controller 410 performs the process of S303 and S304 again. Then, when the relationship between the load and the deformation amount has been obtained at all necessary angles, the operator inputs an end instruction via the input unit 430. When the end instruction has been inputted (S306: YES), the controller 410 sets, as the level of the remaining strength of this pipe, the lowest level among a plurality of levels of remaining strength obtained in S304 (S307). Then, the controller 410 displays this level of remaining strength of the pipe, on the display unit 420 (S308). Thus, the remaining strength evaluation for the pipe as an evaluation target ends.

As described above, according to the internal pressure loading system 1, remaining strength evaluation is automatically performed, and thus, compared to the procedure shown in FIG. 3, burden on the operator is reduced. By setting the internal pressure loading device 100 to the inner face of the installed pipe, it is possible to easily obtain the relationship between the load and the deformation amount of the pipe. In addition, since the evaluation result is displayed on the display unit 420, the operator can easily know the evaluation result.

In the internal pressure loading system 1 shown in FIG. 6, the internal pressure loading device 100 may not necessarily be provided with the motor 190. In this case, as shown in FIG. 1B, the operator needs to expand/contract the internal pressure loading device 100 by use of the wrench 20. However, since the operator need not select an index for remaining strength on the basis of design information and crack information and remaining strength evaluation is automatically performed, burden on the operator is reduced compared with the procedure shown in FIG. 3.

<Modification 1>

In the internal pressure loading system 1 described above, the operator needs to change the setting angle of the internal pressure loading device 100. However, as shown below, the internal pressure loading device 100 may be configured to be automatically rotated.

It should be noted that a motor 610 and expansion/contraction portions 620 correspond to "first change mechanism" described in claims.

Figure 8A:
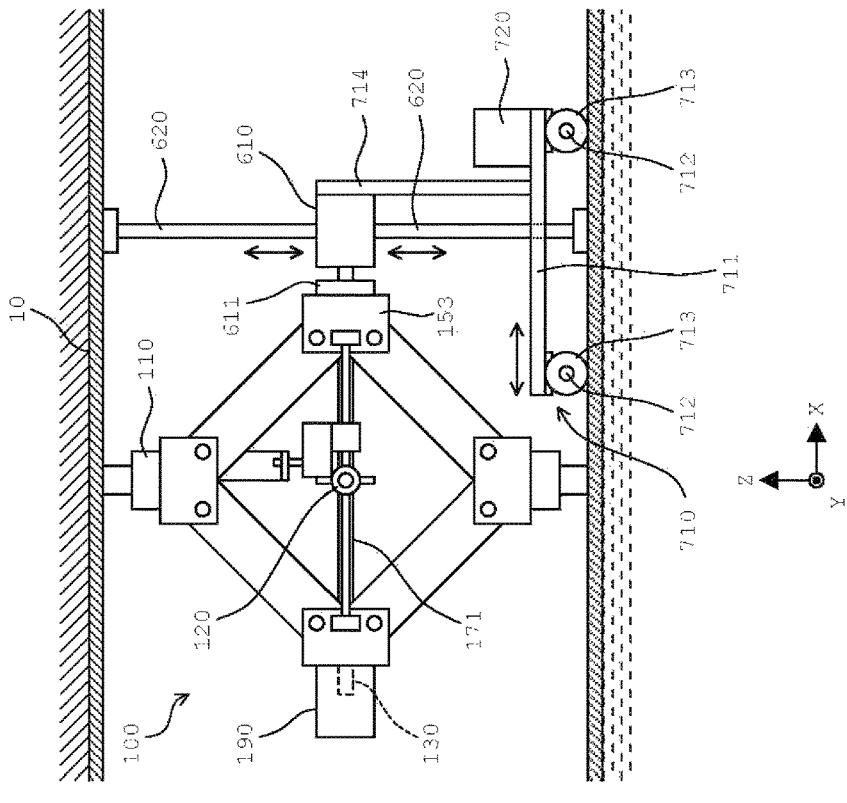
FIG. 8A is a schematic diagram showing a configuration of an internal pressure loading device according to Modification 1.

FIG. 8A is a schematic diagram showing a configuration of the internal pressure loading device 100 according to the present modification. The internal pressure loading device 100 shown in FIG. 8A additionally includes a motor 610 and four expansion/contraction portions 620, compared with the internal pressure loading device 100 shown in FIG. 6. In FIG. 8A, for convenience, only two expansion/contraction portions 620 are shown, and the cable 110*a* for the load meter 110 and the cables 120*a* for the displacement meters 120 are not shown.

The rotation shaft of the motor 610 is set, via a fixture 611, at a side face parallel to the Y-Z plane of the support member 153. At this time, the position of the rotation shaft of the motor 610 matches the position of the long screw 171 when viewed in the X-axis direction. The motor 610 is connected to the driver 500 (see FIG. 6) via a cable (not shown), and is supplied with a drive current from the driver 500. One end of each expansion/contraction portion 620 is set at a side face of the motor 610, and the four expansion/contraction portions 620 extend radially from the motor 610 toward the inner face of the pipe 10. Each expansion/contraction portion 620 is connected to the driver 500 via a cable (not shown), and is supplied with a drive current from the driver 500. By the expansion/contraction portion 620 expanding/contracting, the state of the expansion/contraction portion 620 is switched between a state where the expansion/contraction portion 620 is set at the inner face of the pipe 10, and a state where the expansion/contraction portion 620 is not set at the inner face of the pipe 10.

FIG. 9 is a flow chart showing a procedure of the remaining strength evaluation performed when the internal pressure loading system 1 according to the present modification is used. In the process shown in FIG. 9, compared with the process shown in FIG. 7, S305 and S306 are omitted, S401 is added immediately after S302, and S402 and S403 are added immediately after S304. Hereinafter, only the changed configuration will be described.

The controller 410 selects an index for remaining strength (S302), and then, causes each expansion/contraction portion 620 to expand (S401), thereby to fix the internal pressure loading device 100 relative to the inner face of the pipe 10, as shown in FIG. 8A. Then, when the controller 410 has obtained a level of remaining strength (S304), the controller 410 determines whether levels of remaining strength at all angles have been obtained (S402). When levels of remaining strength at all angles have not been obtained (S402: NO), the controller 410 drives the motor 190 such that the load of the load meter 110 becomes 0, thereby making a state where the internal pressure loading device 100 can be rotated about the X-axis inside the pipe 10. Then, the controller 410 causes the shaft of the motor 610 to be rotated by a predetermined amount. Accordingly, the internal pressure loading device 100 is rotated about the X-axis inside the pipe 10 (S403).

The rotation amount of the motor 610 is controlled on the basis of the time period of application of the drive current to the motor 610, for example.

Thereafter, when levels of remaining strength at all angles have been obtained (S402: YES), the controller 410 sets, as the level of remaining strength of this pipe, the lowest level among the levels of remaining strength obtained in S304 (S307). Thus, according to the present modification, a plurality of results of evaluations performed in the circumferential direction of the pipe can be automatically obtained, and thus, burden on the operator is reduced. In addition, since the remaining strength of the pipe is searched for in the circumferential direction of pipe, the remaining strength of the pipe can be more appropriately evaluated.

<Modification 2>

Further, in Modification 1 of the internal pressure loading system, the internal pressure loading device 100 may be configured to be automatically moved in the longitudinal direction (X-axis direction) of the pipe 10.

It should be noted that a cart 710 and a motor 720 described below correspond to "second change mechanism" described in claims.

Figure 8B:
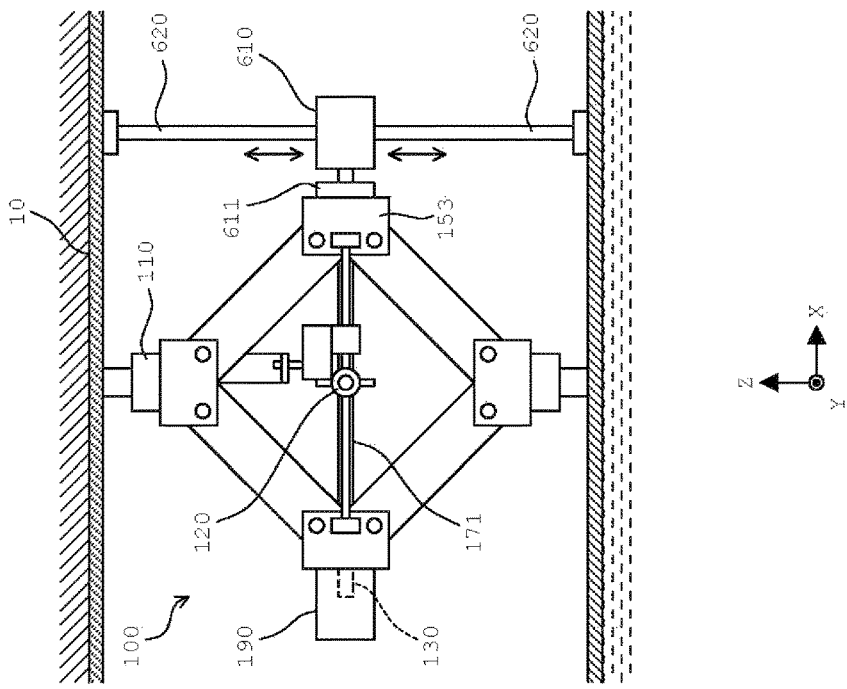
FIG. 8B is a schematic diagram showing a configuration of an internal pressure loading device according to Modification 2.

FIG. 8B is a schematic diagram showing a configuration of the internal pressure loading device 100 according to the present modification. The internal pressure loading device 100 shown in FIG. 8B additionally includes a cart 710 and a motor 720, compared with the internal pressure loading device 100 shown in FIG. 8A.

The cart 710 includes a plate member 711, tires 713, shafts 712 which support the tires 713, and a fixture 714. The rotation shaft of the motor 720 is set at a shaft 712 via a gear (not shown). The motor 720 is connected to the driver 500 (see FIG. 6) via a cable (not shown), and is supplied with a drive current from the driver 500. When the motor 720 is driven, each shaft 712 is rotated, whereby the cart 710 is moved in the X-axis direction. Meanwhile, by the self-holding ability of the motor 720, rotation of the shaft 712 is inhibited, and movement of the cart 710 in the X-axis direction is inhibited. The fixture 714 connects the plate member 711 of the cart 710 to a side face on the X-axis positive side of the motor 610.

FIG. 10 is a flow chart showing a procedure of the remaining strength evaluation performed when the internal pressure loading system 1 according to the present modification is used. In the process shown in FIG. 10, compared with the process shown in FIG. 9, S501 to S503 are added immediately before S307. Hereinafter, only the changed configuration will be described.

When levels of remaining strength at all angles have been obtained (S402: YES), the controller 410 determines whether levels of remaining strength have been obtained at all positions in the X-axis direction (S501). When levels of remaining strength have not been obtained at all positions in the X-axis direction (S501: NO), then, the controller 410 sets the load applied to the load meter 110 to be 0, and then causes each expansion/contraction portion 620 to be contracted. Further, the controller 410 causes the shaft of the motor 720 to be rotated by a predetermined amount. As a result, all components including the internal pressure loading device 100 shown in FIG. 8B are moved in the X-axis direction inside the pipe 10 (S503). The rotation amount of the motor 720 is controlled on the basis of the time period of application of the drive current to the motor 720, for example.

When the movement of the internal pressure loading device 100 in the X-axis direction ends (S503), the controller 410 causes the expansion/contraction portion 620 to be expanded again (S401). Then, at a different position in the X-axis direction, a plurality of levels of remaining strength are obtained again, with the setting angle of the internal pressure loading device 100 varied. Then, until levels of remaining strength are obtained at all positions in the X-axis direction, the internal pressure loading device 100 is moved in the X-axis direction. The movement in the X-axis direction of the internal pressure loading device 100 is performed such that the internal pressure loading device 100 is sequentially located at the end position on the X-axis negative side of the pipe, the center position in the longitudinal direction (X-axis direction) of the pipe, and the end position on the X-axis positive side of the pipe, for example.

Thereafter, when levels of remaining strength have been obtained at all positions in the X-axis direction (S501: YES), the controller 410 sets, as the level of remaining strength of this pipe, the lowest level among the levels of remaining strength obtained in S304 (S307).

As described above, according to the present modification, not only in the circumferential direction of the pipe, but also in the longitudinal direction of the pipe, a plurality of evaluation results can be automatically obtained. Thus, burden on the operator is reduced. In addition, since the remaining strength of the pipe is searched for in the entire the pipe, the remaining strength of the pipe can be further appropriately evaluated.

<Modification 3>

In the embodiments described above, the pipe as an evaluation target is visually observed from inner side thereof, whereby crack information of the pipe is obtained. However, operation of confirming cracks through visual observation requires a lot of effort and some cracks could be unnoticed. Further, in a state where the pipe is buried in the soil, a crack that has occurred on the outer face of the pipe cannot be confirmed. A crack that has occurred on the outer side of the pipe could be a big factor in remaining strength evaluation for the pipe.

Therefore, the present modification further uses a technique of detecting a crack that has occurred in the pipe, on the basis of an output value from the internal pressure loading device 100.

Figure 11A:
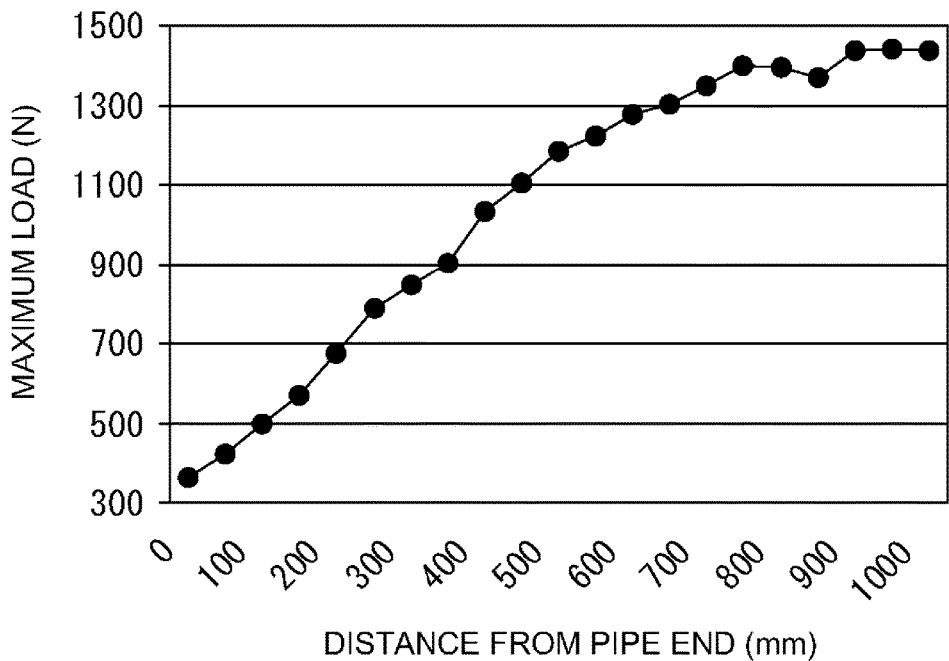
FIG. 11A is a graph showing a result of measurement of the relationship between the load necessary for contracting a sound PVC pipe in the radial direction by 1 mm, and the distance from an end of the pipe according to Modification 3.

FIG. 11A is a graph showing a result of measurement performed by the internal pressure loading device 100 regarding the relationship between the load (vertical axis) necessary for contracting a sound (intact) PVC (polyvinyl chloride) pipe in the radial direction by 1 mm, and the distance (horizontal axis) from an end of the pipe. The PVC pipe used in the measurement was a straight pipe having an outer diameter of 424 mm, a thickness of 12 mm, an inner diameter of 400 mm, and a length of 2000 mm. In the measurement, while a load was applied to the inner side of the pipe by the grounding member 161, 162 of the internal pressure loading device 100, the contracted amount of the pipe was measured by the displacement meter 120, and the load at the time when the contracted amount reached 1 mm was obtained. The measurement position was varied by a 100 mm interval from the end of the pipe. Hereinafter, for convenience, the load that is necessary for contracting a pipe in the radial direction by 1 mm will be referred to as "maximum load".

Figure 11B:
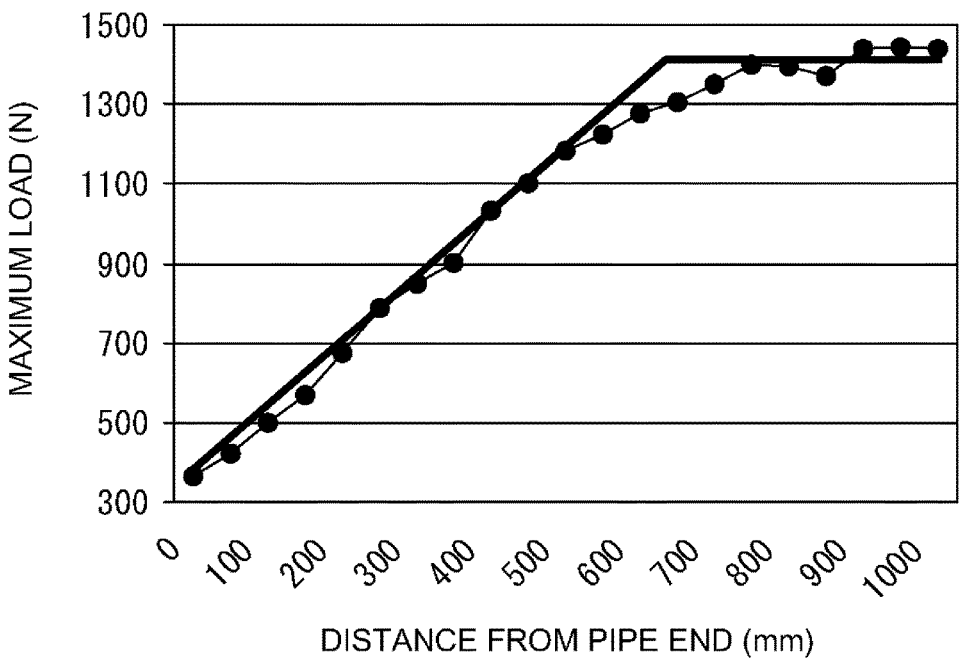
FIG. 11B is the graph in FIG. 11A to which an approximate straight line is added.

As shown in FIG. 11A, the maximum load increased from the end of the pipe toward the center of the pipe, and after the position about 700 mm from the end of the pipe, became substantially constant up to the center of the pipe. FIG. 11B is the graph of FIG. 11A to which an approximate straight line is added. This approximate straight line is symmetric with respect to the center (position at 1000 mm from the end of the pipe) of the pipe, because of the symmetry of the pipe. Therefore, when a plurality of the pipes 10 are coupled together as shown in the upper drawing in FIG. 12A, the maximum load is expected to vary as shown in the lower drawing in FIG. 12A.

In this case, assuming that the left-end pipe 10 is disposed at the entrance of a path, and, for example, if a crack 10a has occurred in the third pipe 10 from the entrance of the path as shown in FIG. 12B, the maximum load can be locally reduced at the position that corresponds to the crack 10a. This is because the strength is reduced due to the crack 10a and the pipe 10 is more likely to be deformed. Therefore, by measuring the maximum load at a predetermined interval (100 mm interval, for example) for the entire length of the pipe 10, it becomes possible to detect a crack that has occurred in the pipe 10.

For example, in a case where a range W1 in which the maximum load is substantially constant includes a measurement position, then, if the maximum load at the measurement position is smaller in a step-like manner than the maximum loads at measurement positions before and after the measurement position, it can be determined that a crack exists at the measurement position. In this case, if the maximum load at the measurement position is smaller than the maximum loads at the measurement positions before and after the measurement position, and the difference between the maximum load at the measurement position and the maximum loads at the measurement positions before and after the measurement position is greater than a predetermined threshold, it can be determined that a crack exists at the measurement position.

In a case where a range W2 in which the maximum load varies includes a measurement position, then, for example, if the maximum load at the measurement position is smaller in a step-like manner than the average value of the maximum loads at measurement positions before and after the measurement position, it can be determined that a crack exists at the measurement position. In this case, if the maximum load at the measurement position is smaller than the average value of the maximum loads at the measurement positions before and after the measurement position, and the difference between the maximum load at the measurement position and the average value of the maximum loads at the measurement positions before and after the measurement position is greater than a predetermined threshold, it can be determined that a crack exists at the measurement position.

By the above technique, a crack that has occurred in the pipe 10 can be detected. For example, by using the internal pressure loading device 100 of a self-propelled type shown in FIG. 8B, even when a plurality of the pipes 10 are coupled together, it is possible to smoothly detect a crack in each pipe 10. The crack thus detected serves as crack information to be referred to in the evaluation of the embodiments described above. Accordingly, the remaining strength of the pipe 10 can be further accurately evaluated.

Although measurement results regarding a PVC pipe are shown FIGS. 11A and 11B, it can be expected that pipes of other kinds such as reinforced concrete pipe, reinforced plastic composite pipe, and ductile cast iron pipe also exhibit properties similar to that shown in FIG. 11A and 11B. In FIGS. 11A and 11B, the maximum load near the center of the pipe is greater than that at the end of the pipe. This could be attributed to the fact that the end of the pipe is a free end and thus is less likely to be restricted. Thus, as in the case of the PVC pipe used in the measurement, pipes of other kinds that have free ends can be expected to exhibit properties similar to that shown in FIG. 11A and 11B.

In the description above, the presence/absence of a crack is detected on the base of an approximate straight line. However, the relationship between the maximum load and the distance from an end of the pipe may not be necessarily approximated by a straight line. For example, for each kind of a pipe, the relationship between the maximum load and the distance from an end of the pipe is approximated by a unique curve. Then, if the maximum load is deviated from the approximate curve, it may be determined that a crack has occurred in the pipe.

Alternatively, with respect to a sound pipe 10 that does not have a crack among the pipes 10 that are coupled together as shown in FIG. 12A, the relationship between the maximum load and the distance from an end of the pipe is measured, and then, the property based on this measurement result may be used in crack detection in other pipes 10. In general, the pipe 10 that is disposed at the entrance of a path is less likely to receive a large load, and thus, such a pipe 10 is often in a sound state without a crack. Therefore, if absence of cracks in the pipe 10 disposed at the entrance of the path is confirmed through visual observation, then, with respect to this pipe 10, the relationship between the maximum load and the distance from an end of the pipe is measured, and then, the property based on this measurement result may be used in detection of cracks in other pipes 10. According to this method, a crack in each pipe 10 is detected by use of the relationship between the maximum load and the distance from an end of the pipe, the relationship being obtained under the same laying condition. Thus, a crack in each pipe can be more accurately detected.

<Modification 4>

In the present modification, a crack in a pipe is detected by a technique that is different from Modification 3. More specifically, in the present modification, a crack that has occurred in a pipe is detected by use of the slope of a straight line that represents the relationship between the load applied to the pipe and the deformation amount of the pipe.

The inventor of the present application conducted various measurements on concrete pipes (hume pipe) in order to derive a crack detection technique according to the present modification. Each concrete pipe used in the measurements was a straight pipe having an inner diameter of 400 mm, a thickness of 36 mm, and a length of 500 mm. A crack (break) about 100 mm long was caused to occur in the concrete pipe, and the internal pressure loading device 100 was set at the length position at which the crack had occurred. The length position at which the crack occurred was 250 mm from an end of the concrete pipe, that is, the center position of the concrete pipe. While the load was varied by the internal pressure loading device 100 thus set, the relationship between the load and the deformation amount was measured.

The crack condition is shown in Table 1 below. In the condition below, "0°" means that the position at which to apply a load by the internal pressure loading device 100 matches the position of the crack, and "90°" means that the position at which to apply a load by the internal pressure loading device 100 and the position of the crack are shifted from each other by 90° in the circumferential direction of the pipe. "Inner face" means that the crack has occurred in the inner face of the pipe, and "outer face" means that the crack has occurred in the outer face of the pipe. "Depth" means the depth of the crack. In condition (1), it is required to use a concrete pipe without any crack, i.e., a sound concrete pipe. In condition (10), the crack reaches a reinforcing bar provided inside the concrete pipe, and the reinforcing bar is exposed from the crack.

TABLE 1

| Condition | Crack Depth | Position | |
|---|---|---|---|
| (1) | 0 mm | none | |
| (2) | 5 mm | Inner face | 0° |
| (3) | 5 mm | Inner face | 90° |
| (4) | 5 mm | Outer face | 0° |
| (5) | 5 mm | Outer face | 90° |
| (6) | 10 mm | Inner face | 0° |
| (7) | 10 mm | Inner face | 90° |
| (8) | 10 mm | Outer face | 0° |
| (9) | 10 mm | Outer face | 90° |
| (10) | 20 mm | Inner face | 0° |

Figure 13A:
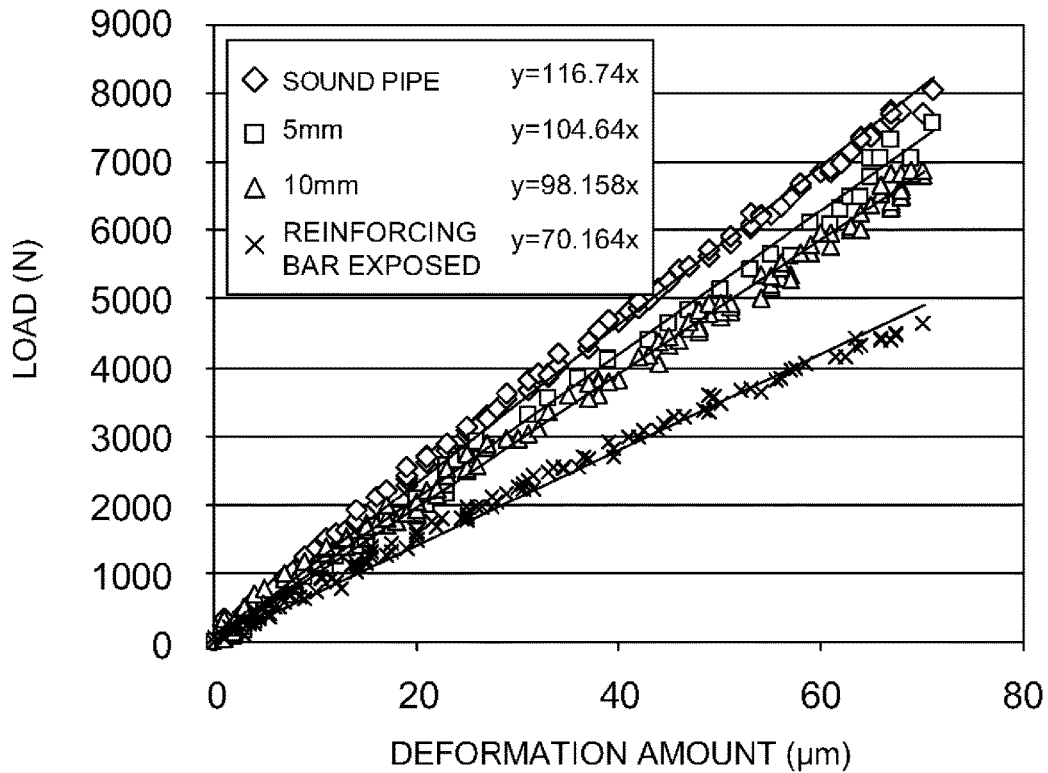
FIG. 13A shows a result of measurement of the relationship between the load and the deformation amount with respect to a sound concrete pipe and concrete pipes each having a crack in the inner face thereof according to Modification 4.

FIG. 13A shows a measurement result regarding a concrete pipe in which a crack occurred in the inner face thereof. The crack condition of this case corresponds to conditions (1), (2), (6), and (10) in Table 1. The positions of the cracks are all "0°", that is, the loading position matches the position of the crack. In FIG. 13A, "sound pipe" corresponds to condition (1), "reinforcing bar exposed" corresponds to condition (10). "5 mm" and "10 mm" correspond to conditions (2) and (6), respectively.

With reference to FIG. 13A, in both of the state without a crack and the state with a crack, it is seen that the relationship between the load and the deformation amount shows a linear characteristic. In addition, it is seen that the deeper the crack is, the smaller the slope of the straight line is. FIG. 13A also shows a function of y (vertical axis) in terms of x (horizontal axis) representing the straight line obtained under each condition. In condition (10), it is seen that, due to the exposure of the reinforcing bar, the deformation characteristic of the concrete pipe has significantly changed compared to that in conditions (2) and (6). If a crack penetrates the concrete pipe, the deformation characteristic can still significantly change.

Figure 13B:
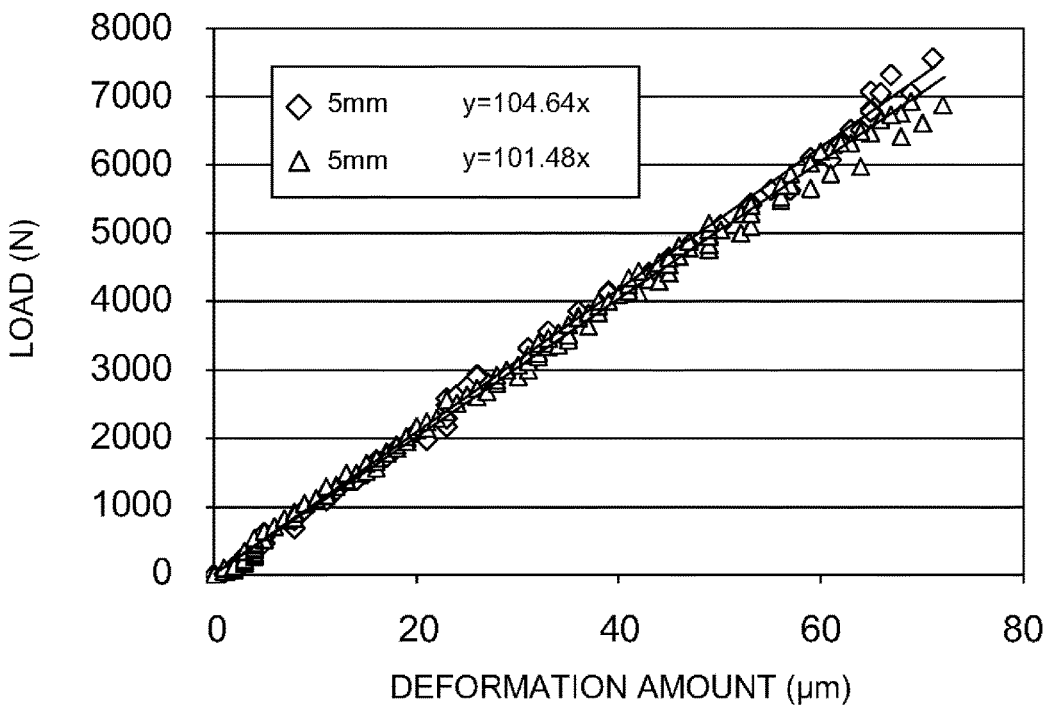
FIG. 13B shows a result of measurement of the relationship between the load and the deformation amount when the load is applied at different positions in the circumferential direction in concrete pipes each having a crack therein according to Modification 4.

FIG. 13B shows a measurement result obtained when the crack condition was condition (2), (3) in Table 1. In each of conditions (2) and (3), the depth of the crack is 5 mm. In condition (2), the loading position matches the position of the crack, and in condition (3), the loading position and the position of the crack are shifted from each other by 90° in the circumferential direction of the pipe.

With reference to FIG. 13B, it is seen that, between condition (2) and condition (3), the straight lines each representing the relationship between the load and the deformation amount match each other. From this, it is seen that, when the depths of cracks are the same, even if measurement positions are different in the circumferential direction, substantially the same relational straight lines can be obtained. That is, it is seen that the shift between the loading position and the measurement position in the circumferential direction of the pipe substantially does not have influence on the relational straight line representing the state of the crack.

Figure 14A:
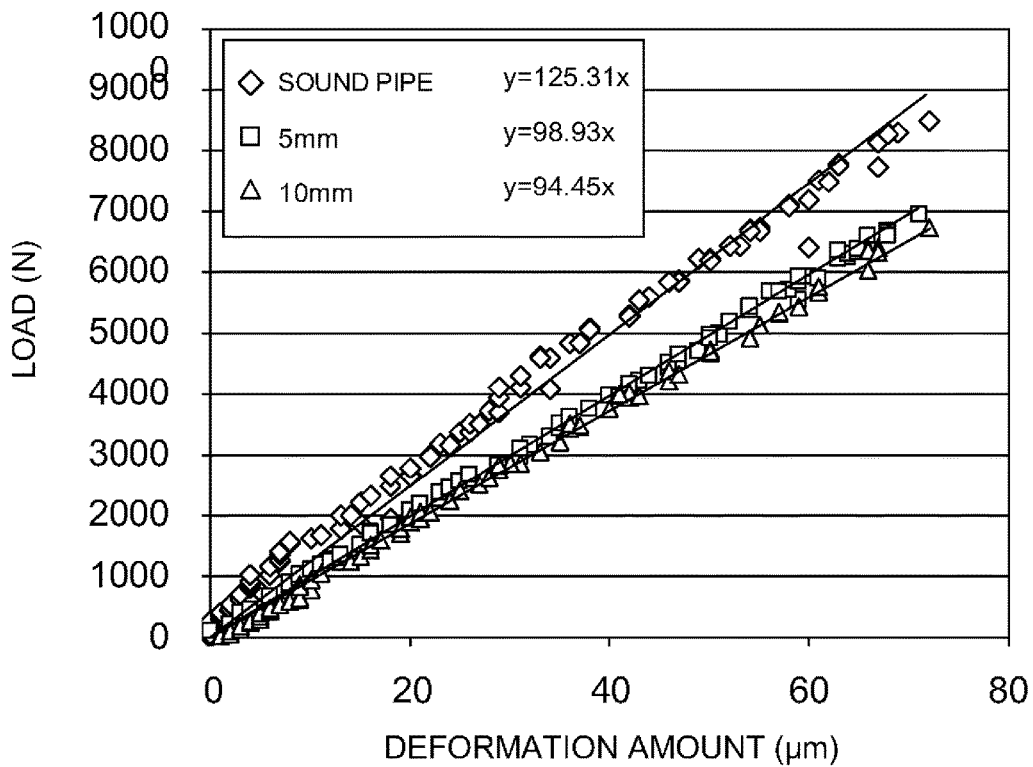
FIG. 14A shows a result of measurement of the relationship between the load and the deformation amount with respect to a sound concrete pipe and concrete pipes each having a crack in the outer face thereof according to Modification 4.

FIG. 14A shows a measurement result obtained when the crack condition was condition (1), (4), (8) in Table 1. Here, with conditions (4) and (8) applied, cases where the cracks were in the outer face of the pipe were evaluated. The positions of the cracks are both "0°", that is, the loading position matches the position of the crack. In FIG. 14A, "sound pipe" corresponds to condition (1), and "5 mm" and "10 mm" correspond to conditions (4) and (8), respectively.

With reference to FIG. 14A, in both of the state without a crack and the state with a crack, it is seen that the relationship between the load and the deformation amount shows a linear characteristic. That is, also in the case where a crack exists in the outer face of the pipe, the relationship between the load and the deformation amount can be approximated by a straight line. In addition, from the measurement result shown in FIG. 14A, it is seen that the deeper the crack is, the smaller the slope of the straight line becomes. FIG. 14A also shows a function of y (vertical axis) in terms of x (horizontal axis) representing the straight line obtained under each condition.

From the measurement results described above, it is seen that, not only in the case where a crack has occurred in the inner face of a pipe, but also in the case where a crack has occurred in the outer face of the pipe, the slope of the straight line representing the relationship between the load and the deformation amount becomes small compared to that of a sound pipe. In addition, it is seen that even when the position at which to apply the load and the position at which to detect the deformation amount are shifted in the circumferential direction of the pipe, the straight line representing the relationship between the load and the deformation amount substantially does not change. Therefore, if the deformation amount of the pipe is detected while the load is varied at a predetermined position in the length direction of the pipe by the internal pressure loading device 100, and then, the slope of the straight line representing the relationship between the load and the deformation amount is obtained, it is possible to determine whether a crack has occurred at that position.

For example, for each of the kind and laying condition of the pipe, a range of the slope for a case where a crack has occurred is set in advance. Then, on the basis of whether this range includes the slope of a straight line representing the relationship between the load and the deformation amount that have been actually measured, the presence/absence of a crack can be determined. In this case, in accordance with the size (length, depth) of the crack, the range of the slope may be further subdivided. Accordingly, not only whether a crack has occurred in the pipe but also the size of the crack can be determined. Alternatively, for each kind and laying condition of the pipe, a slope for a sound pipe is set in advance. Then, on the basis of whether the slope of a straight line representing the relationship between the load and the deformation amount that have been actually measured is smaller than the slope for the sound pipe, the presence/absence of a crack can be determined. In this case, for example, on the basis of the ratio of the actually measured slope relative to the slope for the sound pipe, the size of the crack can be determined.

Also in the technique according to the present modification, similar to Modification 3 described above, by use of the internal pressure loading device 100 of a self-propelled type shown in FIG. 8B, for example, even when a plurality of the pipes 10 are coupled together, it is possible to smoothly detect a crack in each pipe 10. The crack thus detected serves as crack information to be referred to in the evaluation of the embodiments described above. Accordingly, the remaining strength of the pipe 10 can be further accurately evaluated.

Although measurement results regarding a concrete pipe are shown in FIG. 13A to FIG. 14A, it can be expected that pipes of other kinds such as PVC pipe, reinforced plastic composite pipe, and ductile cast iron pipe also exhibit properties similar to those shown in FIG. 13A and FIG. 14A. Therefore, also with respect to pipes of other kinds, by the internal pressure loading device 100 performing measurement regarding the relationship between the load and the deformation amount, it is possible to determine the presence/absence of a crack.

In the present modification, by causing the pipe to be deformed only about several 10 µm, it is possible to detect the presence/absence of a crack. Thus, application of a load for detecting a crack causes neither damage nor new defect in the pipe.

Figure 14B:
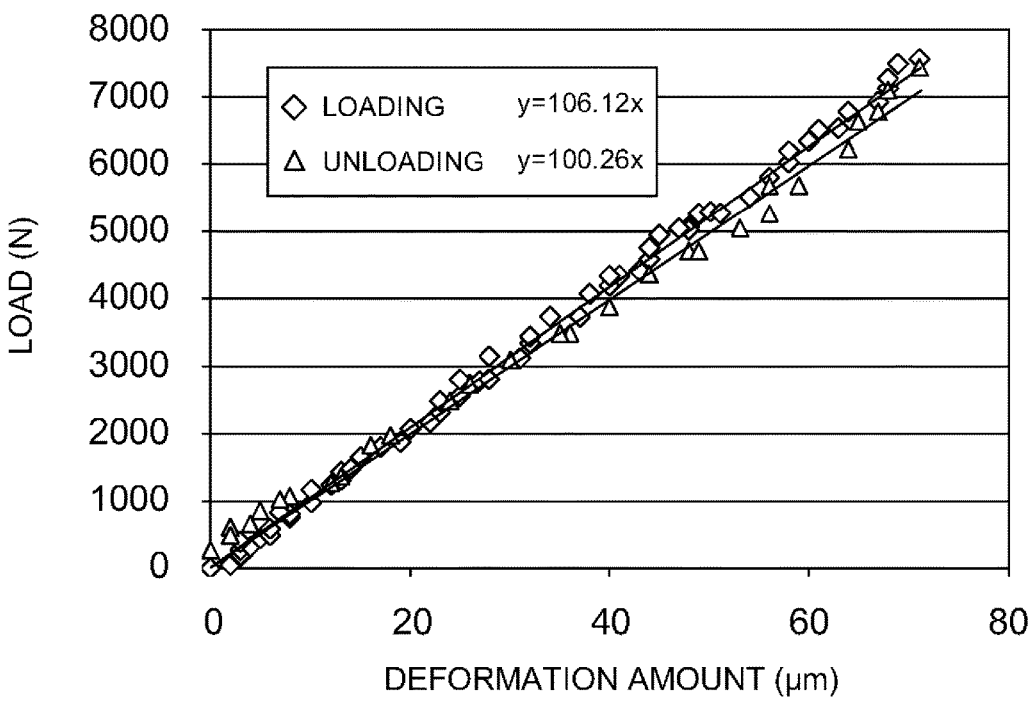
FIG. 14B shows a result of measurement of the relationship between the load and the deformation amount by performing loading and unloading on a concrete pipe having a crack therein according to Modification 4.

FIG. 14B shows a measurement result obtained by the internal pressure loading device 100 performing the following measurement. That is, a concrete pipe having a crack condition of depth 20 mm, inner face, and 90° was caused to receive a load that was gradually increased up to about 8000 N and then gradually reduced, and the deformation amount of the concrete pipe during this loading and unloading was measured. The residual of the deformation amount between the loading and unloading was 4 µm. Thus, even when the deformation amount is increased to a maximum of 70 µm, the residual is very small. Therefore, even when the presence/absence of a crack is evaluated by increasing the deformation amount up to about 70 µm as in the present modification, evaluation can be performed in the plasticity region close to the elasticity region (elastoplasticity region) of the pipe, and thus, neither damage nor new defect is caused in the pipe.

In the present modification, it is sufficient that the slope of the straight line representing the relationship between the load and the deformation amount is obtained. Therefore, it is not necessary to apply to the pipe a load that deforms the pipe up to 70 µm. For example, in the case of the properties of the concrete pipes shown in FIG. 13A and FIG. 14A, the load to be applied to the pipe is preferably suppressed to a magnitude that produces the deformation amount of about 40 µm, so as to prevent damage of the pipe as much as possible. This also applies to pipes of other kinds.

<Other Modifications>

Embodiments of the present invention have been described. However, the present invention is not limited to the embodiments described above, and the embodiments of the present invention can also be modified in various ways.

For example, in the internal pressure loading device 100 described above, the grounding member 161, 162 has the shape as shown in FIG. 2, but the length in the X-axis direction of the grounding member 161, 162 may be longer than that shown in FIG. 2. With this configuration, the region of the pipe receiving the load at the inner side thereof from the internal pressure loading device 100 is extended in the longitudinal direction of the pipe, and thus, the pipe can be more effectively pushed. Accordingly, the deformation amount of the pipe can be more appropriately detected. Furthermore, this configuration can prevent the internal pressure loading device 100 from tilting in the X-axis direction when the internal pressure loading device 100 is set inside the pipe, and thus, it is possible to more accurately apply a load to the inside of the pipe, to obtain the deformation amount inside the pipe.

The internal pressure loading device 100 described above may be provided with a lighting device for illuminating the inside of the pipe and a camera for taking an image of the inside of the pipe. Then, even in a case where it is difficult to view with eyes the inside of the pipe, such as when the diameter of the pipe is small and it is difficult for an operator to enter the pipe, it is possible to smoothly obtain crack information. Especially when the internal pressure loading device 100 is of a self-propelled type as in Modification 2 shown in FIG. 8B, this configuration allows observation of the inside of the pipe by means of camera images while advancing the internal pressure loading device 100 in the longitudinal direction of the pipe. Accordingly, the characteristic of the pipe such as a crack inside the pipe can be appropriately determined.

The internal pressure loading device 100 described above may be provided with a level. Then, when the operator sets the internal pressure loading device 100 inside the pipe, the operator can easily align the direction in which the grounding members 161 and 162 are arranged, with the vertical direction, and can easily align the direction in which the two displacement meters 120 are arranged, with the horizontal direction.

In the embodiments described above, crack information is used as the information indicating the characteristic of the pipe. However, not only the crack information but also other information regarding scratch, flaw, etc. may further be used. In the embodiments described above, the internal pressure loading device 100 is configured such that the direction in which the grounding members 161 and 162 are arranged and the direction in which the two displacement meters 120 are arranged are perpendicular to each other. However, not limited thereto, the angle between the direction in which the two displacement meters 120 are arranged and the direction in which the grounding members 161 and 162 are arranged may be shifted from 90 degrees. Also in this case, the amount by which the width of the pipe is reduced as a result of application of a load can be detected by the displacement meters 120.

In the internal pressure loading system 1 described above, an index for remaining strength is selected, and then, on the basis of the selected index for remaining strength and the obtained relationship of the load and the deformation amount, the level of remaining strength is obtained. However, not limited thereto, the level of remaining strength may be obtained through calculation. In this case, for example, the information processing device 400 creates an index for remaining strength through a simulation process performed by analytical software, using inputted design information and crack information as parameters. Then, the information processing device 400 applies to the created index the relationship of the load and the deformation amount obtained by the internal pressure loading device 100, and thereby obtains the level of remaining strength of the pipe as an evaluation target. Without creation of an index for remaining strength, the remaining strength of the pipe as an evaluation target may be obtained through calculation by using, as parameters, inputted design information and crack information as well as the loads and deformation amounts obtained by the internal pressure loading device 100.

In the internal pressure loading system 1 described above, the information processing device 400 obtains the level of remaining strength of the pipe on the basis of obtained loads and deformation amounts. However, not limited thereto, the processes up to obtaining loads and deformation amounts may be performed only by the information processing device 400. Then, obtaining the remaining strength level on the basis of the obtained loads and deformation amounts and on the basis of design information and crack information may be performed by another information processing device. In this case, for example, the operator transfers the loads and deformation amounts obtained by the information processing device 400, via a storage medium or a network to another information processing device. Then, the another information processing device obtains the level of remaining strength of the pipe on the basis of the loads and deformation amounts.

In the embodiments described above, remaining strength evaluation is performed on the pipe in a state of being buried in the soil. However, the present invention is not necessarily applied only to a pipe in a state of being buried in the soil. For example, also in a case where a pipe coated by a heat insulating material or painting is laid in a high place, the present invention can be applied as appropriate.

In addition to the above, various modifications can be made as appropriate to the embodiments of the present invention without departing from the scope of the technical idea defined by the claims.

What is claimed is:

1. An evaluation method for evaluating a remaining strength of a pipe, the evaluation method comprising:
    applying a load to an inner face of the pipe in a first direction;
    detecting a deformation amount of the pipe in a second direction which is different from the first direction; and
    evaluating a remaining strength of the pipe on the basis of relationship between the load and the deformation amount, wherein
    the remaining strength of the pipe is evaluated in a state where the pipe is buried in soil.

2. The pipe evaluation method according to claim 1, wherein
    the remaining strength of the pipe is evaluated by comparing the relationship between the load and the deformation amount with an index for remaining strength evaluation, the index being based on unique information, a characteristic, and a burying condition of the pipe.

3. The pipe evaluation method according to claim 2, wherein
    the characteristic of the pipe includes a state of a crack in the pipe, and
    the burying condition includes a condition regarding a depth at which the pipe is buried and soil texture around the pipe.

4. The pipe evaluation method according to claim 1, wherein
    an angle between the first direction and the second direction is 90 degrees.

5. The pipe evaluation method according to claim 1, wherein
    a plurality of evaluation results of the remaining strength of the pipe are obtained by shifting the first direction and the second direction in a circumferential direction of the pipe, and
    on the basis of an evaluation result having a lowest remaining strength evaluation among the obtained plurality of evaluation results, the remaining strength of the pipe is set.

6. The pipe evaluation method according to claim 5, wherein
    a plurality of evaluation results of the remaining strength of the pipe are obtained, by shifting the first direction and the second direction in the circumferential direction of the pipe while shifting a position at which to apply the load and a position at which to detect the deformation amount in a longitudinal direction of the pipe, and
    on the basis of an evaluation result having a lowest remaining strength evaluation among the obtained plurality of evaluation results, the remaining strength of the pipe is set.

7. The pipe evaluation method according to claim 1, wherein
    prior to actual evaluation, relationship between a load and a deformation amount is detected from another pipe;
    a remaining strength of the another pipe is evaluated through a compression test;
    an index for pipe remaining strength evaluation is set on the basis of the relationship between the load and the deformation amount in the another pipe and a result of the evaluation of the remaining strength of the another pipe, and
    on the basis of the set index, the remaining strength of the pipe in the actual evaluation is evaluated.

8. The pipe evaluation method according to claim 1, wherein
    at a measurement position in a longitudinal direction of the pipe, a load for deforming the pipe by a predetermined amount is obtained, and
    on the basis of a magnitude of the obtained load, whether a crack has occurred in the pipe at the measurement position is determined.

9. The pipe evaluation method according to claim 1, wherein
    at a measurement position in a longitudinal direction of the pipe, a straight line representing relationship between the load applied to the pipe and the deformation amount of the pipe is obtained, and
    on the basis of the obtained straight line, whether a crack has occurred in the pipe at the measurement position is determined.

10. The pipe evaluation method according to claim 9, wherein
    on the basis of a slope of the straight line, whether a crack has occurred in the pipe at the measurement position is determined.

11. A measurement device to be set at an inner face of a pipe, the measurement device comprising:
    a pressurizing unit configured to apply a load to an inner face of the pipe in a first direction; and
    a detection unit configured to detect a deformation amount of the pipe in a second direction which is different from the first direction, wherein
    the pipe is evaluated in a state where the pipe is buried in soil.

12. An evaluation system configured to evaluate a remaining strength of a pipe, the evaluation system comprising:
    a measurement device including: a pressurizing unit configured to apply a load to an inner face of the pipe in a first direction; and a detection unit configured to detect a deformation amount of the pipe in a second direction which is different from the first direction; and
    an information processing unit configured to evaluate the remaining strength of the pipe, on the basis of relationship between the load applied by the pressurizing unit and the deformation amount detected by the detection unit, wherein
    the remaining strength of the pipe is evaluated in a state where the pipe is buried in soil.

13. The pipe evaluation system according to claim 12, further comprising:
    an input unit; and
    a display unit, wherein
    the information processing unit evaluates the remaining strength of the pipe, on the basis of the relationship between the load and the deformation amount obtained via the measurement device, and on the basis of unique information, a characteristic, and a burying condition of the pipe set via the input unit, and causes the display unit to display an evaluation result.

14. The pipe evaluation system according to claim 12, wherein the measurement device further includes a first change mechanism configured to shift the first direction and the second direction in a circumferential direction of the pipe, and on the basis of respective relationships between the load and the deformation amount obtained with the first direction and the second direction shifted by the first change mechanism, the information processing unit obtains a plurality of evaluation results of the remaining strength of the pipe, and on the basis of an evaluation result having a lowest remaining strength evaluation among the obtained plurality of evaluation results, the information processing unit determines the remaining strength of the pipe.

15. The pipe evaluation system according to claim 14, wherein the measurement device further includes a second change mechanism configured to shift a position at which to apply the load and a position at which to detect the deformation amount in a longitudinal direction of the pipe, and on the basis of respective relationships between the load and the deformation amount obtained with the first direction and the second direction shifted by the first change mechanism while the position at which to apply the load and the position at which to detect the deformation amount are shifted by the second change mechanism in the longitudinal direction of the pipe, the information processing unit obtains a plurality of evaluation results of the remaining strength of the pipe, and on the basis of an evaluation result having a lowest remaining strength evaluation among the obtained plurality of evaluation results, the information processing unit determines the remaining strength of the pipe.

* * * * *